(12) United States Patent
Eryilmaz et al.

(10) Patent No.: US 11,655,490 B2
(45) Date of Patent: May 23, 2023

(54) PROCESS FOR PREPARING A DYED BIOPOLYMER AND PRODUCTS THEREOF

(71) Applicant: Sanko Tekstil Isletmeleri San. Ve Tic. A.S., Inegol-Bursa (TR)

(72) Inventors: Jitka Eryilmaz, Inegol-Bursa (TR); Ece Senel, Inegol-Bursa (TR); Nejdiye Gunes, Inegol-Bursa (TR); Zeynep Kardes, Inegol-Bursa (TR); Özgür Cobanoglu, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 115 days.

(21) Appl. No.: 16/377,622

(22) Filed: Apr. 8, 2019

(65) Prior Publication Data

US 2019/0309335 A1    Oct. 10, 2019

(30) Foreign Application Priority Data

Apr. 9, 2018   (EP) .................... 18166269

(51) Int. Cl.
| | | |
|---|---|---|
| *C12P 19/04* | (2006.01) | |
| *C12N 1/16* | (2006.01) | |
| *C12N 1/20* | (2006.01) | |
| *C12P 39/00* | (2006.01) | |
| *D06P 1/00* | (2006.01) | |
| *D06P 1/22* | (2006.01) | |
| *D06M 16/00* | (2006.01) | |
| *C12P 13/04* | (2006.01) | |
| *C12P 17/10* | (2006.01) | |
| *D06N 3/00* | (2006.01) | |
| *D06P 1/50* | (2006.01) | |
| *D06P 1/46* | (2006.01) | |
| *D06P 1/24* | (2006.01) | |
| *D06N 3/02* | (2006.01) | |
| *D06P 5/22* | (2006.01) | |
| *C12P 21/02* | (2006.01) | |
| *C09B 61/00* | (2006.01) | |
| *C12P 17/16* | (2006.01) | |
| *D06P 1/34* | (2006.01) | |
| *D06P 1/48* | (2006.01) | |

(52) U.S. Cl.
CPC .............. *C12P 19/04* (2013.01); *C09B 61/00* (2013.01); *C12N 1/16* (2013.01); *C12N 1/20* (2013.01); *C12P 13/04* (2013.01); *C12P 17/10* (2013.01); *C12P 17/165* (2013.01); *C12P 21/02* (2013.01); *C12P 39/00* (2013.01); *D06M 16/003* (2013.01); *D06N 3/0006* (2013.01); *D06N 3/0018* (2013.01); *D06N 3/0065* (2013.01); *D06N 3/02* (2013.01); *D06P 1/0004* (2013.01); *D06P 1/008* (2013.01); *D06P 1/0016* (2013.01); *D06P 1/0048* (2013.01); *D06P 1/228* (2013.01); *D06P 1/24* (2013.01); *D06P 1/34* (2013.01); *D06P 1/46* (2013.01); *D06P 1/48* (2013.01); *D06P 1/50* (2013.01); *D06P 5/22* (2013.01); *D06N 2203/026* (2013.01); *D06N 2203/028* (2013.01)

(58) Field of Classification Search
CPC . C12P 19/04; C12P 39/00; C12N 1/16; C12N 1/20
See application file for complete search history.

(56) References Cited

U.S. PATENT DOCUMENTS

| | | | |
|---|---|---|---|
| 4,520,103 A | 5/1985 | Ensley, Jr. | |
| 5,817,381 A | 10/1998 | Chen et al. | |
| 5,834,297 A | 11/1998 | Oriel | |
| 6,872,119 B2 | 3/2005 | Brink | |
| 10,294,611 B2 * | 5/2019 | Eryilmaz | ................ D06N 3/12 |
| 2005/0025512 A1 | 2/2005 | Umetsu | |
| 2005/0255126 A1 | 11/2005 | Tsubaki et al. | |
| 2018/0105977 A1 * | 4/2018 | Nugent | .................... D06P 1/34 |

FOREIGN PATENT DOCUMENTS

| | | |
|---|---|---|
| CN | 102 127 576 | 7/2011 |
| CN | 102127576 | 7/2011 |
| CN | 106120384 | 11/2016 |
| CN | 106916861 | 7/2017 |
| CN | 108720032 | 2/2018 |
| CN | 108660794 | 10/2018 |
| CN | 108720032 | 11/2018 |
| EP | 3239373 | 11/2017 |

(Continued)

OTHER PUBLICATIONS

U.S. Appl. No. 15/493,713; U.S. Appl. No. 16/168,938, filed 2017.*

(Continued)

*Primary Examiner* — Ruth A Davis

(74) *Attorney, Agent, or Firm* — Silvia Salvadori

(57) ABSTRACT

The present invention relates to a process for the production of a dyed biopolymer comprising the steps of providing at least one biopolymer-producing microorganism, providing at least one dye-producing microorganism, culturing said at least one biopolymer-producing microorganism to produce at least a biopolymer, and culturing said dye-producing microorganism wherein said dye-producing microorganism produce at least a dye suitable to dye at least part of said biopolymer, whereby a dyed biopolymer is obtained. The present invention also relates to a dyed biopolymer, to process for the production of a dyed composite article comprising at least the dyed biopolymer and to articles comprising the dyed biopolymer.

18 Claims, 6 Drawing Sheets

(56) References Cited

FOREIGN PATENT DOCUMENTS

| | | | | |
|---|---|---|---|---|
| EP | 3239373 A1 | * | 11/2017 | ............... D03D 1/00 |
| GB | 2537144 | | 10/2016 | |
| JP | 06257074 | | 10/1994 | |
| JP | 0987977 | | 3/1997 | |
| JP | H0987977 | | 3/1997 | |
| JP | 10113169 | | 5/1998 | |
| WO | 2016/162657 | * | 10/2016 | |
| WO | 2016162657 | | 10/2016 | |
| WO | 2017186583 | | 11/2017 | |
| WO | 20170186584 | | 11/2017 | |
| WO | 20170203281 | | 11/2017 | |

OTHER PUBLICATIONS

Aviva Rutkin: "Pigment-making microbes could replace dirty synthetic dyes", New Scientist (Jan. 6, 2016).

Hart et al: "Identification of indigo-related pigments produced by *Escherichia coli* containing a cloned Rhodococcus gene".

Han et al: "Optimization of bio-indigo production by recombinant *E. coli* harboring fmo gene", Enzyme and Microbial fecnhology, vol. 42, Issue 7, Jun. 5, 2008, pp. 617-623.

Search report and written opinion dated Jul. 9, 2019 for European Patent application No. EP 19168150.

Search report and written opinion dated Oct. 4, 2018 for priority European Patent application No. EP18166269.

Notice of Opposition filed at the EPO dated Sep. 1, 2022 by Troesch Scheidegger Werner AG for corresponding European patent No. 3553226.

Facts and Arguments filed at the EPO on Sep. 1, 2022 by Troesch Scheidegger Werner AG for corresponding European patent No. 3553226.

Notice of Opposition filed at the EPO dated Sep. 1, 2022 by JG Oppositions Limited for corresponding European patent No. 3553226.

Facts and Arguments filed at the EPO on Sep. 1, 2022 by JG Oppositions Limited for corresponding European patent No. 3553226.

Wikipedia, "Bacterial cellulose", retrieved on Jul. 20, 2022 from "https://en.wikipedia . . org/w/index php?title=Bacterial_cellu_lose &o_Idid=822666629.".

Costa et al., "Review—Bacterial Cellulose: An Ecofriendly Biotextile" International Journal of Textile and Fashion Technology, 2017.

Chan et al., "Development of Tailor-Shaped Bacterial Cellulose Textile Cultivation Techniques for Zero-Waste Design" Clothing and Textiles Research Journal, 2018.

Costa et al., "Dyeing of bacterial cellulose films using plant-based natural dyes" Int. J. Biol. Macromol, 2018.

Mufson, "These Beautiful Silk Scarves Were Created With Bacteria", [cited Aug. 11, 2022].

Luchtman, L. and Siebenhaar, 1. Biodesign Research Project "Living Colour" Published Jan. 21, 2017.

Peters, A. "These gorgeous colors come from dye made by bacteria, not chemicals". Fast Company. Published Oct. 29, 2018.

Budds, D. "This $314 Necktie Is A Biotech Breakthrough". Fast Company. Published Mar. 10, 2017.

Anzilotti, E. "How Modern Meadow Is Fabricating The Animal-Free Leather Of The Future". Fast Company. Published Oct. 11, 2017.

Azeredo et al., "Bacterial Cellulose as a Raw Material for Food and Food Packaging Applications" Frontiers in Sustainable Food Systems, 2019.

Submission of the Patentee dated Apr. 14, 2020 filed during prosecution of the application 19168150.1.

Florea et al., "Engineering control of bacterial cellulose production using a genetic toolkit and a new cellulose-producing strain" PNAS, 2016.

Farris et al., "Pullulan-Based Films and Coatings for Food Packaging: Present Applications, Emerging Opportunities, and Future Challenges" Journal of Applied Polymer Science, 2014.

Monika Faidi, Bachelor Thesis "Feasibility of bacterial cellulose in furniture design", Allto Unversity School of Arts, Design and Architecture Interior Archituecture spring 2017.

Rutkin, Aviva, "Pigment-making microbes could replace dirty synthetic dyes" New Scientist, Jan. 6, 2016.

Exploringtheinvisible.com, "pDENIM" Dec. 9, 2016, [cited Aug. 25, 2022] Available from: [https://explori ngtheinvisible . com/ 2016/ 12/09/pdeni m-towards-a-sustai nable-de nim-grown-entirely-from-bacteria/].

Costa et al., "Production of Bacterial Cellulose by Gluconacetobacter hansenii Using Corn Steep Liquor As Nutrient Sources" frontiers in Microbiology, Val. 8, No. 2027, Oct. 2017.

Ravish, Kumar M, "Chromobacterium violaceum: A rare bacterium isolated from a wound over the scalp" International Journal of Applied and Basic Medical Research, Val. 2, Jan. 2012.

Goers, Lisa et al., "Co-culture systems and technologies: taking synthetic biology to the next level" J. R. Soc. Interface, Val. 11, Jul. 6, 2014.

Amazon, "Edible Butterflies" Sep. 13, 2011, [cited Aug. 29, 2022] Available from: [https://www.amazon.com/Edible-Butterflies%C2% A9-Assorted-Cupcake-Decor ation/d p/8005 MZI RSO?language= en_ US].

Sigalevich et al., "Oxygen-Dependent Growth of the Sulfate-Reducing Bacterium Desulfovibrio oxyclinae in Coculture with *Marinobacter* sp. Strain MB in an Aerated Sulfate-Depleted Chemostat" Applied and Environmental Microbiology, Val. 66, Nov. 1, 2000.

Meng, Shun Lang et al., "Interaction Effects of Temperature, Light, Nutrients, and pH on Growth and Competition of Chlorella vulgaris and *Anabaena* sp Strain PCC" frontiers in Environmental Science, Val. 9, No. 690191, Jul. 16, 2021.

Aharonovich, "Transcriptional response of Prochlorococcus to co-culture with a marine Alteromonas: differences between strains and the involvement of putative infochemicals" The ISME Journal, Val. 10, Apr. 29, 2016.

Rosano et al., "Recombinant protein expression in *Escherichia coli*: advances and challenges" frontiers in Microbiology, Val. 5, No. 172, Apr. 17, 2014.

Yang et al., "Production of Rainbow Colorants by Metabolically Engineered *Escherichia coli*" Advanced Science, Val. 8, May 25, 2021.

Jayabalan, Rasu et al., "A Review on Kombucha Tea-Microbiology, Composition, Fermentation, Bene?cial Effects, Taxicity, and Tea Fungus" Comprehensive Reviews in Food Science and Safety, Val. 13, Jun. 21, 2014.

ed.com, "Grow your own clothes" Mar. 26, 2014, [cited Aug. 29, 2022] Available from: [https://www.ted.com/talks/suzanne_lee_ grow_your_own_clothes/transcript].

* cited by examiner

PROCESS FOR PREPARING A DYED BIOPOLYMER AND PRODUCTS THEREOF

This Non-Provisional Application claims priority to and the benefit of European Patent Application 18166269.3 filed on Apr. 9, 2018, the content of which is incorporated herein by reference in its entirety.

FIELD OF THE INVENTION

The present invention relates to the field of biopolymers, in particular to the field of dyed biopolymers. Specifically, the present invention relates to a process for the production of a dyed biopolymer and articles comprising it.

BACKGROUND OF THE INVENTION

Commercial success of an article largely depends from its aesthetical appearance, in particular in the fields of decorations, accessories, packaging, and in the field of textiles.

For example, success in denim industry largely depends from the recognizable appearance of a fabric, and thus of clothing articles produced with such fabric. Fabric having a unique appearance, have become very popular, in particular because they have a non-standardized, and thus readily distinguishable, aesthetical aspect.

The exterior appearance of a fabric can be modified by using different dyeing and/or finishing techniques.

For example, a "used" or "vintage" or "worn-out" look of the fabric can be achieved by treating the fabric with a finishing process that is generally carried out on the garment or on the fabric. The known finishing processes may use specific chemicals, or mechanical abrasion, such as processes using stone-washing, acid wash, laser treatment and sandblasting.

However, the visible effects and appearance that are obtainable by the known finishing treatments, are limited. Therefore, garments made by different producers are often similar one to another, thus reducing the commercial desirability of the product and the possibility to distinguish a product from those of another producer.

A further disadvantage of traditional stone washing is that the stones can damage the fabric.

International Application PCT/EP2017/059471 (WO 2017/186583 A1), as well as EP3239373A1, both in the name of the present applicant, disclose a process for producing a treated fabric which has a multi-shaded and unique effect, comprising the steps of providing a layer of biopolymer on at least one side of a fabric to provide a composite fabric, dyeing at least part of the composite fabric and finally removing at least part of the dyed biopolymer layer, thus obtaining a fabric dyed with a plurality of shades of color. The biopolymer layer used in the process of WO 2017/186583 A1 allows the production of a fabric having a plurality of shades of color, and provided protection from damages to the fabric. However, the process of WO 2017/186583 A1 is not suitable to impart aesthetical visual effects (such as, for example, multi-shaded and unique effects) to a composite fabric.

In fact, in the process of WO 2017/186583 A1, the removal of at least part of the biopolymer layer is mandatory. Moreover, in the process of WO 2017/186583 A1, the fabric and the biopolymer layer are dyed with conventional methods known in the art, which do not provide, per se, a multi-shaded effect to the composite fabric.

GB2537144A discloses a method for dyeing fabrics using microorganisms whereby the adsorption of dye-containing microorganisms onto textile fibers is improved using carbon sources above a threshold concentration. Dye molecules contained within the microorganism are released from the microorganism and fixed directly and locally to the textile fibers using a heat treatment step. Said heat treatment also deactivates the carrier microorganisms. Suitable synthetic dyes may also be added before, during or after microorganisms have produced dyes but before the dye-releasing heat treatment step.

Document by AVIVA RUTKIN, "Pigment-making microbes could replace dirty synthetic dyes|New scientist", NEW SCIENTIST, 6 Jan. 2016 (2016-01-06) XP055418782, GB ISSN:0262-4079 discloses genetically engineered *E. coli* bacteria that can produce indigo, and the growing of such microbes on garments, to provide said garments with the microbially-produced dye.

JP H09 87977 A discloses a staining technique wherein a cellulosic fiber is treated with an aqueous solution containing a tyrosinase enzyme and a melanin precursor.

SUMMARY OF THE INVENTION

It is an aim of the present invention to solve the above mentioned problems and to provide a process for the production of a dyed biopolymer, suitable to be used in the production of articles, e.g. textile articles. The dyed biopolymer has a multi-shaded appearance, i.e., a distinctive appearance which comprises a plurality of shades of color, which are distributed throughout the biopolymer according to a non-standard, i.e. a random distribution, to avoid obtaining the same distribution of shades reproduced in the same way in different articles, e.g., in two different a composite fabrics.

Another aim of the present invention, is to provide a process for the production of a dyed biopolymer and dyed articles comprising it which are dyed in a non-homogeneous, i.e., a non-uniform, way.

It also is an aim of the present invention to provide a process for the production of a dyed biopolymer and dyed articles comprising it, which are commercially desirable, recognizable and readily distinguishable from other products.

A further aim of the invention is to provide a process that substantially avoids or reduces the environmental costs of known processes, as well as substantially avoids or reduces the use of harsh chemicals with respect to the known manufacturing and dyeing processes, particularly in the textile filed.

These and other aims are achieved by a process according to claim 1, which results in the production of a dyed biopolymer according to claim 4.

The invention also relates to a process for the production of a dyed composite article, comprising the dyed biopolymer, according to claim 5.

The dyed biopolymer may be used in the production of a dyed article according to claim 22.

The dependent claims relate to preferred embodiments of the invention.

DETAILED DESCRIPTION OF THE INVENTION

Figure 1A:
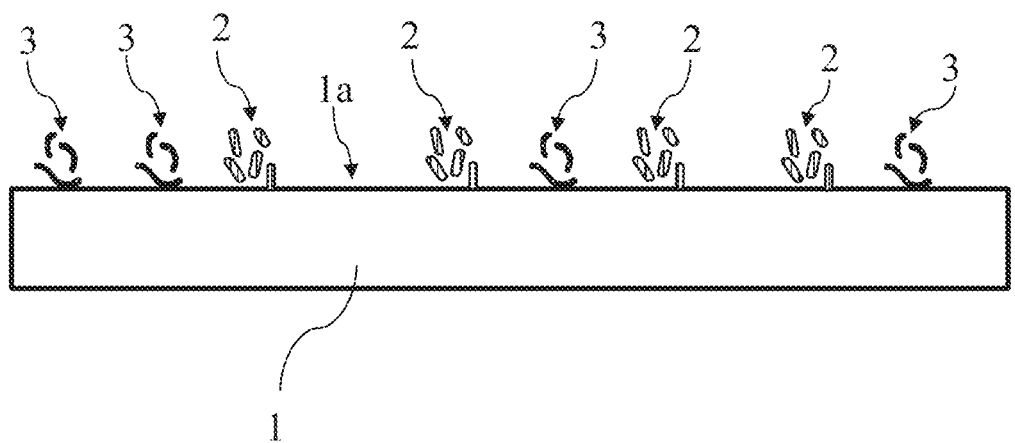
FIGS. 1A and 1B schematically show an embodiment of the process of the present invention wherein the biopolymer-producing microorganisms and the dye-producing microorganisms are provided to a support material together, i.e., at the same time or substantially at the same time.

The present invention relates to a process for the production of a dyed biopolymer comprising the following steps:
- providing at least one biopolymer-producing microorganism,
- providing at least one dye-producing microorganism,
- culturing said at least one biopolymer-producing microorganism to produce at least a biopolymer and
- culturing said dye-producing microorganism wherein said dye-producing microorganism produce at least a dye suitable to dye at least part of said biopolymer, whereby a dyed biopolymer is obtained.

It has been surprisingly found that, through the process of the invention, it is possible to obtain a dyed biopolymer having a non-uniform, i.e. a random and/or non-homogeneous distribution of the dye on its surface. This random, non-homogeneous distribution of the dye, results in a plurality of shades of color which are distributed throughout at least part of the biopolymer layer, according to a unique distribution that cannot be identically reproduced. In other words, through the process of the invention, it is possible to obtain a biopolymer which is at least in part dyed, having an aesthetical appearance that cannot be identically reproduced in a successive biopolymer.

Without being bound to a specific scientific explanation, a possible explanation is that a biopolymer which is produced by living microorganisms, may not be structurally identical to another biopolymer layer, even if it has been produced by the same microorganisms and in the same conditions. Similarly, dye molecules, being produced by living microorganisms, may not be identical in amount and distribution, even if produced by the same microorganisms and in the same conditions.

Advantageously, the process of the invention allows for the production of a dyed biopolymer, which has a distinctive appearance which comprises a plurality of shades of color, i.e., a multi-shaded appearance, which is desirable in many technical fields, such as, for example, the field of decorations (e.g., home decorations), accessories, packaging, and in the field of textiles.

According to embodiments, biopolymer-producing microorganisms and dye-producing microorganism are cultured together, whereby a dyed biopolymer is obtained.

In other words, at least one biopolymer-producing microorganism and at least one dye producing microorganism can be provided and cultured together (i.e., as a co-culture), so that a biopolymer and a dye are produced at the same time (or substantially at the same time), in order to provide a dyed biopolymer.

According to this embodiment of the invention, the process can be defined as a "concurrent" process, wherein the production of the biopolymer and of the dye, i.e. of the dye molecules, occurs during a single step of culturing (e.g., a single incubation). In this case, advantageously, a dyed biopolymer according to the invention can be obtained according to a one culturing step process.

According to embodiments of the process of the invention, at least one biopolymer-producing microorganism is cultured to produce a biopolymer, and at least one dye-producing microorganism is provided to said biopolymer and cultured, to produce at least a dye, to dye at least part of said biopolymer layer, to obtain a dyed biopolymer.

In other words, biopolymer-producing microorganisms can be cultured to provide a biopolymer. Subsequently, at least one dye-producing microorganism can be provided to the biopolymer and cultured to produce a dye, in order to dye at least part of the biopolymer.

According to this embodiment of the invention, the process can be defined as a "consecutive" process, wherein the production of the biopolymer and the production of the dye, i.e., the dye molecules, occur substantially sequentially. In this case, advantageously, it is possible to decide how to distribute the dye-producing microorganisms on the biopolymer.

Preferably, biopolymer-producing microorganisms are not removed from the biopolymer before providing dye-producing microorganisms. In this case, advantageously, the thickness of the biopolymer layer increases because the biopolymer-producing microorganisms are still present in the culture medium and/or in the biopolymer, when the culture of dye-producing microorganisms is provided and cultured onto the undyed biopolymer. In other words, after adding the dye-producing microorganisms, both dye and biopolymer production will continue. Advantageously, without being bound to a specific scientific explanation, it has been observed that, in this case, dye molecules are easily entrapped within the biopolymer.

The present invention also relates to a dyed biopolymer as obtainable with a process according to the invention.

As above mentioned, the dyed biopolymer of the invention has a multi-shaded appearance, which cannot be identically reproduced, and that cannot be obtained using known processes.

The dyed biopolymer of the invention may be, advantageously, used for the production of articles in several technical fields, such as, for example, the field of decorations (e.g., home decorations), accessories, packaging, and in the field of textiles.

According to embodiments, the dyed biopolymer of the invention can be worked into an article (i.e., an object), to obtain an article that essentially consists of, or consists of, the dyed biopolymer of the invention.

For example, the dyed biopolymer of the invention may be tailored into a garment. Other exemplary articles that can be essentially consists of the dyed biopolymer are earrings, necklaces, bags, and fashion accessories.

According to the present description, when an article is defined as "essentially consisting of the dyed biopolymer", it is meant that the essential structure of the article is made by the dyed biopolymer, but other elements of the article may be made of other materials. For example, a earring may be have a decorative portion consisting of the biopolymer of the invention, and a metal clip to secure the earring to a ear of a user.

According to embodiments, the dyed biopolymer of the invention may be produced onto a support material, for example a textile article.

According to an aspect, the present invention also relates to a process for the production of a dyed composite article comprising at least a dyed biopolymer layer according to the invention, comprising the following steps:
a) Providing at least one support material;
b1) providing at least part of the support material with at least one biopolymer-producing microorganism, wherein said microorganism produces at least a biopolymer layer on at least part of the support material; and
b2) providing at least part of the support material with at least one dye-producing microorganism, wherein said microorganism produces at least a dye suitable to dye at least part of said biopolymer layer,
whereby a dyed composite article is obtained.

As above mentioned, it has been surprisingly found that, through the process of the invention, a dyed composite article, for example a fabric, can be obtained, wherein the dyed composite article has a non-uniform, i.e. a random or non-homogeneous distribution of the dye on its surface. As above discussed, this random, non-homogeneous distribution of the dye, results in a plurality of shades of color which are distributed throughout the composite article, namely, throughout at least part of the biopolymer layer, according to a unique distribution that cannot be identically reproduced. In other words, through the process of the invention, a dyed composite article comprising a biopolymer layer can be obtained, wherein at least part of the biopolymer layer is dyed according to a distribution of shades of color that cannot be identically copied or reproduced from a composite article to another.

As above discussed, without being bound to a specific scientific explanation, a possible explanation is that a biopolymer layer according to the invention, being produced by living microorganisms, may not be structurally identical to another biopolymer layer, even if it has been produced by the same microorganisms and in the same conditions, through the same process. Similarly, dye molecules, being, according to the invention, produced by living microorganisms, may not be identical in amount and distribution, even if produced by the same microorganisms and in the same conditions.

It has been observed that, by providing at least part of a support material, for example a textile article, with biopolymer-producing microorganisms and dye-producing microorganisms and culturing said microorganisms, a dyed composite article (e.g., a dyed composite textile article) comprising a dyed biopolymer layer is obtained wherein, advantageously, the biopolymer layer is non-homogeneously dyed, i.e., the dye is not uniformly distributed on the biopolymer layer.

For example, when the support material is a textile article, advantageously, the dyed composite textile article obtained through the process of the invention, presents a unique, multi-shaded, effect, which is not identically reproducible, i.e., which cannot be copied from a textile article to another; in another words, the process of the invention provides dyed textiles where the pattern of the shades of the dye is different in different areas of a fabric and is different in two different garments.

The color distribution and color uniformity can be measured with a spectrophotometer, according to methods that are per se known in the art. A suitable spectrophotometer for measuring color uniformity in a sample of dyed biopolymer is a HunterLAB spectrophotometer. A suitable standard test method that can be used to measure color distribution is "Marks & Spencer C41, Instrumental Colour Measurement of Textiles". Through this method, the distribution of the color (e.g., the non-homogeneous distribution of the color) in a dyed biopolymer or in a dyed composite article may be measured.

In a possible way of measure, in a sample of fabric 10×10 cm the colour intensity is measured in a plurality of regions (i.e., two or more regions) of the sample. The measurements of the color intensity are carried out at different regions (i.e., points) of the sample, that are spaced by 1 cm. If the sample shows regions having different color intensity that are visually identifiable with naked eye, measurements are preferably performed in such regions, for example in the regions that show the highest and the lowest color intensity. When the difference of the value of color intensity between two points of the sample is less than or equal to 20%, preferably less than or equal to 10%, more preferably less than or equal to 1%, the color distribution in the sample is considered homogeneous and uniform, according to HunterLAB Spectrophotometer. A fabric obtained according to the invention method typically shows a difference of color intensity between two points of the sample that is more than 20. In particular, a dyed biopolymer (or a dyed composite article) according to the invention has at least two regions wherein difference in color intensity between said two regions is more than 20%, preferably more than 30%.

Also advantageously, the dye may be provided both to at least part of the biopolymer layer and on at least part of the support material, e.g., a textile article, to provide further aesthetical effects.

According to embodiments, the support material is a dyed support material. In other words, the support material may be colored before being provide with biopolymer-producing microorganisms and/or the dye-producing microorganisms. In this case, advantageously, a great variety of aesthetical effects may be obtained.

Advantageously, according to an aspect of the invention, a dyed composite article according to the invention, comprising a support material and a dyed biopolymer layer, may be used for the production of articles of manufacture in different technical fields.

According to embodiments, the biopolymer-producing microorganisms and the dye-producing microorganisms can be provided to the support material together, i.e., at the same time (or substantially at the same time), or separately, i.e., sequentially.

In other words, according to embodiments, step b1) and step b2) of the process for the production of a dyed composite article of the invention may be carried out together or separately.

Advantageously, when the biopolymer-producing microorganisms and the dye-producing microorganisms are provided to the support material together, i.e., at the same time, the microorganisms are cultured together, to provide the support material with a dyed biopolymer layer.

Advantageously, when the biopolymer-producing microorganisms and the dye-producing microorganisms are provided to the support material separately, i.e., sequentially, biopolymer-producing microorganisms are cultured first, to provide the support material with a biopolymer layer which is not dyed. Subsequently, dye-producing microorganisms are provided to the support material and cultured to provide a dye to at least part of the biopolymer layer, to obtain a composite article including a dyed biopolymer layer.

According to embodiments, step b1) and/or step b2) comprise the steps of contacting at least part of the support material (e.g., a textile article) with at least one culture of microorganisms comprising at least one biopolymer-producing microorganism and at least one culture of microorganisms comprising at least one dye-producing microorganisms and culturing the biopolymer-producing microorganism and the dye-producing microorganisms on said support material.

According to embodiments, the support material, e.g. a fabric, is contacted with biopolymer-producing microorganisms and dye-producing microorganisms, and subsequently the microorganisms are growth (i.e., cultured) as a co-culture, to provide the support material with a dyed biopolymer, usually as a layer.

As used herein, terms "contacted" and "contacting", refer the act of providing or applying one or more culture comprising at least one microorganism to a substrate. For example, the substrate may be an undyed or dyed support material, or an undyed or dyed biopolymer. According to the present invention, cultures comprising microorganisms may be provided or applied to a substrate according to known techniques such as, for example, spraying or pouring.

According to embodiments, a first culture comprising biopolymer-producing microorganisms and a second culture comprising dye-producing microorganisms may be provided at the same time to the support material.

According to embodiments, a culture comprising both biopolymer-producing microorganisms and dye-producing microorganisms may be provided to the support material. In other words, according to embodiments, biopolymer-producing microorganisms and dye-producing microorganisms may be provided as a single culture to the support material (e.g., a textile article) and cultured in a single culture medium on the support material.

As used herein, the term "co-culture" refers to the substantially simultaneous culturing of at least two different microorganisms, optionally onto a support material.

According to this embodiment of the invention, the process can be defined as a "concurrent" process, wherein the production of the biopolymer and of the dye, i.e. of the dye molecules, occurs during a single step of culturing (e.g., a single incubation). In this way, advantageously, according to embodiments, a dyed biopolymer layer may be provided to a support material, to obtain a dyed composite article according to a one-step process.

For example, a support material, e.g., a fabric, may be contacted with a first culture of microorganisms comprising biopolymer-producing microorganisms, and with a second culture comprising dye-producing microorganisms substantially at the same time. Once the support material is contacted with the two cultures, the microorganisms are cultured, to produce the biopolymer and the dye (dye molecules) directly on the support material, thus providing a dyed biopolymer layer to the support material. Accordingly, a dyed composite article, e.g., a dyed composite fabric, can be obtained.

According to embodiments, step b1) comprises the steps of contacting at least part of the support material with at least one culture of microorganisms comprising at least biopolymer-producing microorganisms, and culturing said biopolymer-producing microorganisms to provide at least a biopolymer layer and step b2) comprises the steps of contacting at least part of said biopolymer layer with at least one culture of microorganisms comprising dye-producing microorganisms, and culturing said dye-producing microorganisms to provide at least a dye to at least part of said biopolymer layer.

Advantageously, according to embodiments of the invention, a support material, e.g. a fabric, can be contacted with at least two cultures of microorganisms, for example, with a first culture comprising biopolymer-producing microorganisms and subsequently with a second culture comprising dye-producing microorganisms. In other words, the support material, e.g. a fabric, can be sequentially contacted with at least two different cultures of microorganisms, e.g., with two cultures, each one comprising different microorganisms. For example, the support material can be contacted with a first culture comprising biopolymer-producing microorganisms and subsequently with a second culture comprising dye-producing microorganisms.

According to this embodiment of the invention, the process can be defined as a "consecutive" process, wherein the production of the biopolymer and the production of the dye, i.e., the dye molecules, occur substantially sequentially. For example, a biopolymer layer may be provided by culturing biopolymer-producing microorganisms, optionally onto a support material and, subsequently, a dye may be provided to at least part of said biopolymer layer, to obtain a dyed article according to a two-steps process. When a support material is used, a dyed composite article may be obtained.

For example, a support material, e.g., a fabric may be contacted with a culture of microorganisms, comprising biopolymer-producing microorganisms; once the support material is contacted with the culture of biopolymer-producing microorganisms, biopolymer-producing microorganisms are cultured, to produce a layer of biopolymer directly on the support material, thus providing an undyed composite article, i.e. a composite article comprising a layer of biopolymer which is not dyed, i.e., free from dye molecules.

Subsequently, at least part of the biopolymer layer of the above mentioned undyed composite article may be contacted with a culture of microorganisms, comprising dye-producing microorganisms. Once the biopolymer layer is contacted with the culture of comprising dye-producing microorganisms, the dye-producing microorganisms are cultured, to produce dye molecules directly on the undyed composite article, i.e., directly on the biopolymer layer of the undyed composite article, thus providing a dye to at least part of the biopolymer layer. Accordingly, a dyed composite article, e.g., a dyed composite fabric, can be obtained.

According to embodiments, biopolymer-producing microorganisms are removed from the undyed biopolymer or from the undyed composite article before contacting the undyed biopolymer layer with the culture of comprising dye-producing microorganisms.

In this case, the thickness of the biopolymer layer does not increase during the culturing, i.e., during the incubation, of the dye-producing microorganisms.

According to embodiments, biopolymer-producing microorganisms are not removed from the undyed biopolymer or from the undyed composite article before contacting the undyed biopolymer layer with the culture of comprising dye-producing microorganisms.

In this case, the thickness of the biopolymer layer increases because the biopolymer-producing microorganisms are still present, when the culture of dye-producing microorganisms is provided and cultured onto the undyed biopolymer layer. Also advantageously, without being bound to a specific scientific explanation, it has been observed that, in this case, dye molecules are easily blocked within the biopolymer.

According to an advantageous aspect of the present invention, the incubation time of the biopolymer-producing microorganisms and/or of the dye-producing microorganisms may be selected in order to obtain a biopolymer (e.g., a biopolymer layer) having a predetermined thickness, as well as a predetermined shade of color.

For example, the longer is the time of incubation of biopolymer-producing microorganisms, the thicker is the biopolymer layer obtained, optionally onto a support material.

According to embodiments, dye-producing microorganisms and biopolymer-producing microorganisms are provided in a cell number ratio ranging from 1:1 to 1:10, preferably from 1:4 to 1:5.

According to embodiments, dye-producing microorganisms and biopolymer-producing microorganisms are provided to the support material in a cell number ratio ranging from 1:1 to 1:10, preferably from 1:4 to 1:5.

As used herein, the term "cell number ratio" refers to the ratio between the number of dye-producing microorganisms and the number of biopolymer-producing microorganisms that are provided, optionally to the support material. The number of cells, i.e., the number of microorganisms, in a culture may be determined by known methods.

For example, the number of the cells may be determined by spread plate technique. This method is a known method in microbiology to estimate the cell number. Each bacteria is inoculated in its medium and diluted according to several serial dilutions, and plated in appropriate medium. Plates are incubated and, after incubation, the bacterial colonies are counted and cell number is calculated with the following formula:

$$CFU/ml=(\text{no. of colonies}\times\text{dilution factor})/\text{volume of culture plate}$$

CFU (Colony Forming Unit), is a known unit of measurement used to estimate the number of viable bacteria or fungal cells in a sample. Viable is defined as the ability to multiply via binary fission under controlled conditions.

Advantageously, by varying the ratio, i.e., the cell number ratio, between biopolymer-producing microorganisms and dye-producing microorganism, a great variety of dyed articles and/or dyed composite articles may be obtained, each one having a different aesthetical aspect, i.e., a different distribution of the dye molecules throughout the biopolymer layer.

According to embodiments, step b1) and/or b2) of the process of the invention may be performed more than once.

According to embodiments, for example, the support material may be contacted more than once by one or more culture comprising at least both biopolymer-producing microorganisms and dye-producing microorganisms.

In other words, after that a dyed composite article is obtained by contacting the support material with a culture comprising both biopolymer-producing microorganisms and dye-producing microorganisms and co-culturing said microorganisms, the dyed composite article may be contacted by a further culture comprising both biopolymer-producing microorganisms and dye-producing microorganisms, to provide the dyed composite article with a further dyed biopolymer layer.

Similarly, after that a first dyed biopolymer is obtained, culturing biopolymer-producing microorganisms and dye-producing microorganisms, the dyed biopolymer may be contacted by a culture comprising both biopolymer-producing microorganisms and dye-producing microorganisms, to provide a second dyed biopolymer to the first dyed biopolymer.

Advantageously, cultures comprising both biopolymer-producing microorganisms and dye-producing microorganisms may be the same or may be different from each other (e.g., the cultures may comprise the same microorganisms or different microorganisms, in the same ratio or in different ratios) and the microorganisms may be cultured, optionally onto article support material, in the same conditions or in different conditions.

According to embodiments, support material may be contacted with a first culture comprising biopolymer-producing microorganisms, to provide the support material with a biopolymer layer and by contacting said biopolymer layer with a first culture comprising dye-producing microorganisms, to dye to at least part of said biopolymer layer. The obtained dyed composite article may be contacted by a second culture comprising biopolymer-producing microorganisms, to provide a further biopolymer layer, which is not dyed and that may be, in turn, be contacted by a second culture comprising dye-producing microorganisms, to obtain a further dyed biopolymer layer.

According to embodiments, a first culture comprising biopolymer-producing microorganisms may be cultured to obtain a first undyed biopolymer. The first undyed biopolymer may be contacted a first culture comprising dye-producing microorganisms, to dye to at least part of said biopolymer. The obtained dyed biopolymer may be contacted by a second culture comprising biopolymer-producing microorganisms, to provide a further biopolymer, which is not dyed and that may be, in turn, be contacted by a second culture comprising dye-producing microorganisms, to obtain a further dyed biopolymer.

Advantageously, the first and the second culture comprising biopolymer-producing microorganisms, as well as and the first and the second culture comprising dye-producing microorganisms, may comprise the same or different microorganisms, and the microorganisms may be cultured, optionally onto article support material, in the same or in different conditions.

According to embodiments, a support material may be provided with a first dyed biopolymer layer by co-culturing biopolymer-producing and dye-producing microorganisms onto the support material, and then may be provided with a second dyed biopolymer layer by culturing first biopolymer producing microorganisms and subsequently culturing dye-producing microorganisms, to obtain the second dyed biopolymer layer.

According to embodiments, a first dyed biopolymer may be obtained by co-culturing biopolymer-producing and dye-producing microorganisms. The obtained dyed biopolymer may be contacted by a second culture comprising biopolymer-producing microorganisms, to provide a further biopolymer, which is not dyed and that may be, in turn, be contacted by a second culture comprising dye-producing microorganisms, to obtain a further dyed biopolymer.

According to embodiments, a support material may be provided with a first dyed biopolymer layer by culturing biopolymer producing microorganisms first, onto the support material, to provide the support material with a biopolymer layer, and subsequently by culturing dye-producing microorganisms, onto said biopolymer layer, to obtain the first dyed biopolymer layer. Subsequently, a second dyed biopolymer layer may be provided by co-culturing biopolymer-producing and dye-producing microorganisms onto said first dyed biopolymer layer.

According to embodiments, a first dyed biopolymer may be obtained by culturing biopolymer producing microorganisms first, to provide a undyed biopolymer and, subsequently, by culturing dye-producing microorganisms, onto said biopolymer, to obtain the first dyed biopolymer. Subsequently, a second dyed biopolymer layer may be provided by co-culturing biopolymer-producing and dye-producing microorganisms onto said first dyed biopolymer layer.

According to embodiments, a support material may be provided with a first dyed biopolymer layer, by co-culturing biopolymer-producing and dye-producing microorganisms onto the support material, and then the support material may be provided with a second dyed biopolymer layer by a second step of co-culturing of biopolymer-producing and dye-producing microorganisms.

According to embodiments, a first dyed biopolymer may be obtained by co-culturing biopolymer-producing and dye-producing microorganisms. The obtained dyed biopolymer may be contacted by a second co-culture of biopolymer-producing and dye-producing microorganisms to provide a further dyed biopolymer.

According to embodiments, a support material may be provided with a first dyed biopolymer layer by culturing biopolymer producing microorganisms first, onto the support material, to provide the support material with a biopolymer layer, and subsequently by culturing dye-producing microorganisms, onto said biopolymer layer, to obtain the first dyed biopolymer layer. Subsequently, a second dyed biopolymer layer may be provided by sequentially culturing biopolymer producing microorganisms first, to obtain a second biopolymer layer, and then culturing dye-producing microorganisms, to dye the second biopolymer layer.

According to embodiments, a first dyed biopolymer may be obtained by culturing biopolymer-producing microorganisms and dye-producing microorganisms sequentially or at the same time. A second dyed biopolymer may be provided onto said first dyed biopolymer by culturing on the first biopolymer (layer) suitable amount of biopolymer-producing microorganisms and dye-producing microorganisms. The biopolymer-producing microorganisms and dye-producing microorganisms may be cultured on the first biopolymer sequentially or at the same time.

As used herein, the term "biopolymer layer", refer to an amount of at least one biopolymer that is produced by a microorganism, optionally on support material, as defined in the present application. For example, a textile article, including its fibers, may act as a support for the biopolymer. The amount of biopolymer may be present on article support material in many different ways; namely, the biopolymer does not necessarily be present as a continuous layer coating the entire external surface of the support material. The biopolymer layer may be an amount of biopolymer partially extending within the support material and partially covering the surface of the support material. For example, the biopolymer layer may be an amount of biopolymer partially extending in the fibers of a textile article and partially covering the surface of the article. The layer in the following figures is a schematic representation that does not limit the scope of the application.

As used herein, the term "biopolymer" refers to a polymer that can be produced by a microorganism, i.e. to a "microbial polymer".

As used herein, the term "microbial" refers to something that relates to or is characteristic of a microorganism. For example, the term "microbial biopolymer" refers to a biopolymer which can be produced by a microorganism.

As used herein, the term "microorganism" refers to small unicellular or multicellular living organisms that are too small to be seen with naked eye but are visible under a microscope, and encompasses bacteria, yeast, fungi, viruses and algae. As used herein, the term "microorganism" encompasses not genetically modified (i.e. wild type) microorganisms and genetically modified microorganism as well.

For example, a microorganism can be genetically modified in order to produce a biopolymer, or a dye molecule, which is not produced by the same microorganism when it is not genetically modified (i.e., when it is a wild type microorganism).

According to embodiments, a microorganism can be genetically modified in order to produce both a biopolymer and a dye molecule.

According to embodiments, the biopolymer is selected from a sugar-based biopolymer, preferably microbial cellulose, and an amino acid-based biopolymer, preferably microbial collagen, or a mixture thereof.

As used in the present description, the term "sugar-based biopolymer" encompasses linear and branched polysaccharides, variants and derivatives thereof. An exemplary sugar-based biopolymer according to the present invention is microbial cellulose.

As used in the present description, the term "amino-acid based biopolymer" encompasses linear and branched polypeptides, variants and derivatives thereof. An exemplary amino acid-based biopolymer according to the present invention is microbial collagen.

According to embodiments of the invention, the biopolymer, i.e., the microbial biopolymer is selected from the group consisting of microbial cellulose, microbial collagen, microbial cellulose/chitin copolymer, microbial silk, and mixtures thereof. These biopolymers are known per se in the art.

Accordingly, a biopolymer and/or a biopolymer layer, as defined herein, may comprise one or more microbial biopolymers selected from microbial cellulose, microbial collagen, microbial cellulose/chitin copolymer, microbial silk, and mixtures thereof.

For example, microbial cellulose can be produced by culturing strains of *Acetobacter* bacteria, such as strains of *Acetobacter xylinum*, and/or by culturing strains of *Gluconacetobacter*, such as strains of *Gluconacetobacter hansenii*.

For example, microbial collagen can be produced by culturing bacterial strains of *Bacillus, Pseudomonas, Streptococcus* or bacterial strains which have been genetically modified to obtain modified strains that produce collagen.

Advantageously, bacterial collagen can be produced to provide an artificial leather-like material, such as, for example, "artificial leather" or "artificial skin", wherein the main structural component of "leather" and "skin" is collagen, in particular, type I collagen, in the form of strong fibrils.

For example, microbial cellulose/chitin copolymer can be produced by culturing strains of *Acetobacter xylinum* which have been genetically modified to obtain modified strains that produce bacterial cellulose/chitin copolymer.

According to embodiments of the invention, the biopolymer producing microorganisms are a mixture of wild type and genetically modified microorganisms.

According to embodiments, the biopolymer, i.e., the microbial biopolymer, is selected from microbial cellulose (e.g. bacterial cellulose), microbial collagen or mixtures thereof.

According to embodiments, the dye, namely the dye that is produced by dye-producing microorganisms, is selected from indigo dye, indigoid dye, and pigment dye and mixture thereof.

Preferably, the dye is indigo dye, and it is produced by a microorganism that is able to produce indigo.

As used herein, the term "indigoid" refers to dye molecules that are indigo-derivatives.

As used herein, the term "pigment dye" refers to dye molecules that are not indigo-derivatives.

According to embodiments, the indigoid dye is selected from any indigoid dye, such as, for example, 6,6'-dibromoindigo, 5-bromoindigo, 5,5'-dibromoindigo, 5,7,5',7'-tetrabromoindigo, 4,5,7,4',5'-pentabromoindigo, 4,5,6,4',5',6'-hexabromoindigo, 7,7'-dimethylindigo, 4,5,4',5'-tetrachloroindigo, and mixtures thereof.

The above mentioned indigoid dyes have to be intended as non-limiting examples of indigoid dyes suitable to be used in the present invention.

According to embodiments, the pigment dye is selected from melanin, anthraquinone, xanthomonadin, indigoidine, astaxanthin, canthaxantin, cycloprodigiosin, granadaene, heptyl-prodigiosin, prodigiosin, pyocyanin, rubrolone, scytonemin, staphyloxanthin, tryptathrin, undecylprodigiosin, violacein, zeaxanthin, ankaflavin, lycopene, monascorubramin, naphtoquinone, riboflavin, rubropunctatin, β-carotene, torularhodin and mixtures thereof.

The above mentioned pigment dyes have to be intended as non-limiting examples of pigment dyes suitable to be used in the present invention.

As above mentioned, the dye is preferably indigo dye.

According to embodiments, the support material may be selected from paper, cardboard, wood, glass, plastic, and a textile article. According to embodiments, the support material is a textile article.

According to embodiments, the support material is not a textile article.

According to embodiments, the textile article is selected from a fiber, a yarn, a fabric and a garment. According to embodiments, the textile article comprises hydrophilic fibers and/or hydrophilic yarns.

Advantageously, when the textile article comprises hydrophilic fibers, the culture medium of the microorganisms provided onto the textile article is absorbed by the textile article, thus providing nutrients to the microorganisms and ingredients for the synthesis of the biopolymer layer and the dye, directly on the textile article.

According to embodiments of the invention, hydrophilic fibers are natural fibers. For example, natural fibers comprise cotton, wool, flax, kenaf, ramie, hemp, and mixtures thereof.

According to embodiments of the invention, hydrophilic fibers are synthetic fibers. For example, synthetic yarns comprise synthetic fibers selected from polyester, rayon, nylon, lycra and mixtures thereof.

In embodiments, synthetic fibers, or synthetic yarns may be treated (i.e. finished) in order to provide synthetic fiber or synthetic fibers having hydrophilic properties.

In exemplary embodiments of the invention, synthetic fibers and yarns are elastomeric fibers and yarns.

Suitable elastomeric yarns are yarns containing elastomeric fibers. An "elastomeric fiber" is a fiber made of a continuous filament or a plurality of filaments which have an elongation at break of at least 100%, independent of any crimp. Break elongation may be measured e.g. according to ASTM D2256/D2256M-10(2015). An "elastomeric fiber" is a fiber that after being stretched to twice its length and held for one minute at said length, will retract to less than 1.5 times its original length within one minute of being released.

According to preferred embodiments, the textile article is a fabric, preferably a woven fabric, more preferably a denim fabric.

According to an embodiment, when the textile article is a woven fabric, the warp yarns, and/or the weft yarns have a linear density ranging from 118.2 tex (5/1 Ne) to 5.91 tex (100/1 Ne), preferably from 19.7 tex (30/1 Ne) to 8.44 tex (70/1 Ne); more preferably the linear density of warp yarns is from 13.13 tex (45/1 Ne) to 10.754 tex (55/1 Ne), wherein "tex" is a known count unit used in textile field and refer to the mass per unit length of textile yarns and threads (1 tex=$10^{-6}$ kg·$m^{-1}$), and wherein "Ne" is the English cotton number that is a known count unit used in the textile field.

According to a preferred embodiment, a woven fabric suitable for use in the invention comprises warp yarns and weft yarns woven together, and has a front side and a back side, wherein said warp yarns and at least one plurality of weft yarns form a base layer of said woven fabric, and wherein a plurality of warp yarns and/or at least one plurality of weft yarns forms an additional layer of loop portions, for example droopy loop portions, or yarn under portions or over portions, on at least one of the sides of said woven fabric.

According to embodiments of the invention, the textile article is a fabric, preferably a woven fabric; at least part of the fabric is provided with at least a microbial cellulose-producing microorganism, to provide at least part of the fabric with a microbial-cellulose layer, and at least with an indigo dye-producing microorganism, to provide indigo dye to at least part of the microbial cellulose layer. Accordingly, a dyed composite fabric comprising a microbial cellulose layer, wherein at least part of the microbial cellulose layer is indigo dyed, is obtained.

According to embodiments of the invention, at least part of the support material is provided with at least a microbial cellulose-producing microorganism, to provide at least part of the support material with a microbial-cellulose layer, and at least with an indigo dye-producing microorganism, to provide indigo dye to at least part of the microbial cellulose layer.

According to embodiments, a dyed composite article according to the invention comprises a support material and microbial cellulose layer, wherein at least part of the microbial cellulose layer is indigo dyed.

According to embodiments of the invention, a fabric, e.g., a woven fabric, may be contacted by a culture of microorganisms comprising at least a microbial cellulose-producing microorganism and at least one indigo dye-producing microorganism, so that the microbial cellulose and the indigo dye are produced directly on the surface of the fabric.

According to embodiments of the invention, a support material may be contacted by a culture of microorganisms comprising at least a microbial cellulose-producing microorganism and at least one indigo dye-producing microorganism, so that the microbial cellulose and the indigo dye are produced directly on the surface of the support material.

According to embodiments, a fabric may be contacted with a culture of microorganisms comprising microbial cellulose-producing microorganisms, to be provided with a microbial cellulose layer, i.e., to obtain a composite fabric comprising a microbial cellulose layer. Subsequently, at least part of the microbial cellulose layer of the composite fabric may be contacted with a culture comprising indigo dye-producing microorganisms, to dye at least part of the microbial cellulose layer with indigo dye.

According to embodiments, a support material may be contacted with a culture of microorganisms comprising microbial cellulose-producing microorganisms, to be provided with a microbial cellulose layer, i.e., to obtain an undyed composite article comprising a microbial cellulose layer. Subsequently, at least part of the microbial cellulose layer of the composite article may be contacted with a culture comprising indigo dye-producing microorganisms, to dye at least part of the microbial cellulose layer with indigo dye.

According to embodiments, the biopolymer-producing microorganism and/or the dye-producing microorganism is selected from bacteria, algae, yeast, fungi and mixtures thereof.

According to embodiments, the biopolymer-producing microorganism and/or the dye-producing microorganism is a not genetically modified microorganism or a genetically modified microorganism.

According to embodiments, the biopolymer-producing microorganism is selected from biopolymer-producing bacteria, biopolymer-producing algae, and mixture thereof, wherein biopolymer-producing bacteria are selected from *Gluconacetobacter, Aerobacter, Acetobacter, Achromobacter, Agrobacterium, Azotobacter, Salmonella, Alcaligenes, Pseudomonas, Rhizobium, Sarcina* and *Streptoccoccus, Bacillus* genus, genetically modified *Escherichia coli*, and mixtures thereof, and wherein biopolymer-producing algae are selected from *Phaeophyta, Rhodophyta* and *Chrysophyta*, and mixture thereof.

The above mentioned biopolymer-producing bacteria and biopolymer-producing algae have to be intended as non-limiting examples of biopolymer-producing bacteria and biopolymer-producing algae suitable to be used in the present invention.

For example, biopolymer-producing bacteria may be *Gluconacetobacter hansenii, Acetobacter xylinum* or mixtures thereof.

According to embodiments, the dye-producing microorganism is selected from dye-producing bacteria, dye-producing fungi and mixture thereof. Preferably dye-producing bacteria are selected from *Chromobacterium violaceum, Serratia marcescens, Chriseobacteium* sp., *Staphylococcus aureus, Streptomyces* sp., *Vibrio* sp., *Corynebacterium* genus, genetically modified *Escherichia coli*, and mixtures thereof. Preferably, dye-producing fungi are selected from *Penicillium, Talaromyces, Fusarium, Scytallidium, Trametes, Xanthomonas, Streptomyces, Aspergillus* and mixtures thereof.

The above mentioned dye-producing bacteria and dye-producing fungi have to be intended as non-limiting examples of dye-producing bacteria and dye-producing fungi suitable to be used in the present invention.

For example, indigo-producing genetically modified *Escherichia coli*, i.e. recombinant *E. coli* are known from the patent number U.S. Pat. No. 4,520,103, the patent number U.S. Pat. No. 5,834,297 and from the scientific papers "Optimization of bio-indigo production by recombinant *E. coli* harboring fmo gene", G H. Han et al (2008), Enzyme and Microbial Technology 42: 617-623, and "Identification of indigo-related pigments produced by *Escherichia coli* containing a cloned Rhodococcus gene", Hart, S., K. R. Koch, and D. R. Woods, 1992, J. Gen. Microbiol. 138:211-216.

According to embodiments, the process for the production of a dyed biopolymer of the invention further comprises a step of washing the dyed biopolymer to remove the biopolymer-producing microorganisms, and/or the dye-producing microorganisms.

According to embodiments, the process for the production of a dyed biopolymer of the invention further comprises a step of drying the dyed biopolymer.

According to embodiments, the process of the invention further comprises a step c. of washing said dyed composite article obtained after said step b1) and/or said step b2), to remove said biopolymer-producing microorganisms, and/or said dye-producing microorganisms.

According to embodiments, the process of the invention further comprises a step of drying said dyed composite article obtained after said step b1) and/or said step b2) and/or said step c. of washing.

The present invention also relates to a dyed article comprising a dyed biopolymer according to the invention.

According to embodiments, the dyed article essentially consists of, or consists of, the dyed biopolymer of the invention.

In this case, the support material is not used.

According to embodiments, a dyed article essentially consisting of, or consisting of, the dyed biopolymer of the invention may be selected from an article for home decoration, a personal accessory, a packaging article, and a textile article.

For example, a garment may essentially consist of, or consist of, the dyed biopolymer of the invention.

For example, a bag may essentially consist of, or consist of, the dyed biopolymer of the invention.

According to embodiments, the dyed article further comprises a support material; in other words, according to embodiments, the dyed article may be a dyed composite article, namely an article comprising a support material and a dyed biopolymer (e.g., a dyed biopolymer layer) according to the invention.

According to embodiments, the support material is selected from paper, cardboard, wood, glass, plastic and a textile article.

According to embodiments, the support material is a textile article. When the support material is a textile material, a dyed composite textile article can be obtained.

According to embodiments, when the support material is a textile article, it is preferably selected from a fiber, a yarn, a fabric and a garment. In this case, through the process of the invention, a dyed composite textile article can be obtained. Namely, such a dyed composite textile article may be a dyed composite fiber, a dyed composite yarn, a dyed composite fabric or a dyed composite garment.

Dyed composite fibers according to the invention may be used in the production of dyed composite yarns; dyed composite yarns may be used in the production of dyed composite fabrics and dyed composite fabrics may be used in the production of dyed composite garments.

Preferably, a dyed composite fabric may be obtained through the process of the invention.

According to embodiments, the dyed article comprising a dyed biopolymer according to the invention may be an article for home decoration, a personal accessory, a packaging article, or a textile article.

According to embodiments, the dyed article comprising a dyed biopolymer according to the invention may be a earring, a necklace, a bag, or a fashion accessory. Such article may optionally include a support material; in other words, such articles may be dyed composite articles.

For example, the dyed article of the invention may be a packaging article. For example, the support material may be paper, cardboard, or mixtures thereof. For example, a paper or cardboard support layer may be provided with a dyed biopolymer layer, according to the invention. The obtained dyed composite paper or cardboard may be used to produce an article for packaging, for example a box, wherein the dyed biopolymer layer is the external visible surface of the box.

According to embodiments, the dyed article comprising a dyed biopolymer according to the invention, may be a dyed textile article, preferably a garment, more preferably a garment selected from jeans, shirts, garments using a denim fabric, sport garments and casual garments.

According to embodiments, the dyed article is a dyed composite textile article including a support material, and the dyed composite textile article may be selected from jeans, shirts, garments using a denim fabric, sport garments and casual garments.

According to embodiments, a dyed composite fabric as obtainable with the process of the invention is suitable to be included into a garment, to provide a garment which, at least in part, comprises a dyed composite fabric as obtainable through the process of the invention.

Exemplary embodiments of the invention will be now discussed making reference to the Figures; such figures have to be intended as a schematic illustration of exemplary and non-limiting embodiments of the present invention.

In particular, FIGS. 1A-1B and 2A-2C, show embodiments of the process for the production of a dyed composite article according to the invention. In such Figures, reference is made to a fabric as support material; however, as above discussed, different support material may be used, such as, for example, paper, cardboard, wood, glass, plastic, as well as textile articles different from a fabric.

Figure 1B:
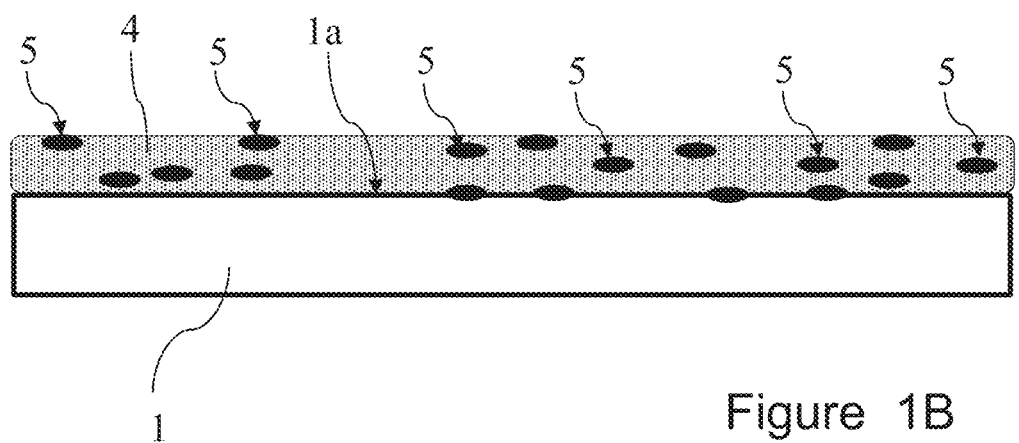

FIGS. 1A and 1B schematically show an embodiment of the process for the production of a dyed composite article of the present invention, wherein the biopolymer-producing microorganisms 2 and the dye-producing microorganisms 3 are provided to the support material 1 together, i.e., substantially at the same time.

In the present FIGS. 1A-1B and 2A-2C, the exemplary support material 1 is a textile article, in particular, a fabric 1.

Preferably, biopolymer-producing microorganisms 2 are *Gluconacetobacter* bacteria, which produce bacterial cellulose.

Preferably, dye-producing microorganisms 3 are recombinant *Escherichia coli*, i.e., genetically modified *Escherichia coli*. Recombinant *Escherichia coli* can produce, for example, indigo and/or indigoid dyes such as Tyrian purple (i.e., 6,6'-dibromoindigo). Dye-producing *Escherichia coli* are known in the art.

In FIG. 1A, the support material 1 is a textile article, in particular, a fabric 1, preferably a woven fabric. The fabric 1, shown according to a cross-sectional view, is contacted both with biopolymer-producing microorganisms 2, preferably *Gluconacetobacter* bacteria and dye-producing microorganisms 3, preferably dye-producing recombinant *Escherichia coli*.

According to the embodiment shown in FIG. 1A, the biopolymer-producing microorganisms 2 and dye-producing microorganisms 3 are provided together on the first side 1a of the fabric 1.

According to embodiments, a first culture comprising biopolymer-producing microorganisms 2 and a second culture comprising dye-producing microorganisms 3 may be provided onto the first side 1a of the fabric 1 substantially at the same time. The biopolymer-producing microorganisms 2 and the dye-producing microorganisms 3 may be subsequently cultured to provide the fabric with a dyed biopolymer layer.

According to embodiments, the biopolymer-producing microorganisms 2 and dye-producing microorganisms 3 may be provided as a culture of microorganisms, i.e., as a single culture comprising both biopolymer-producing microorganism 2 and dye-producing microorganisms 3 in the same culture medium. In this case, the single culture comprising both biopolymer-producing microorganisms 2 and dye-producing microorganisms 3 comprises required nutrients for both biopolymer-producing and dye-producing microorganisms. For example, the culture medium of said single culture may be obtained as a mixture of the two media used for the two microorganisms' growth and production.

Cultures comprising microorganisms may be provide onto the first side 1a of the fabric 1 by conventional methods, such as spraying or pouring.

After that both biopolymer-producing microorganisms 2 and dye-producing microorganisms 3 have been provided onto the first side 1a of the fabric 1, the fabric is incubated, preferably at a temperature ranging from 20° C. to 40° C., to allow the production of a biopolymer and a dye, directly on the first side 1a of the fabric 1.

Preferably, the biopolymer is bacterial cellulose.
Preferably, the dye is indigo.

For example, bacterial cellulose can be produced by culturing strains of *Acetobacter* bacteria, such as strains of *Acetobacter xylinum*, and/or by culturing strains of *Gluconacetobacter*, such as strains of *Gluconacetobacter hansenii*.

For example, indigo can be produced by genetically modified *Escherichia coli*. According to embodiments, the biopolymer-producing microorganisms 2 and dye-producing microorganisms 3 are selected to provide an indigo-dyed bacterial cellulose layer.

At the end of the incubation, a dyed composite article, i.e., a dyed composite fabric, is provided, which is shown in FIG. 1B.

The dyed composite article is subsequently optionally washed to remove the residual microorganisms, and dried.

FIG. 1B shows a support material, i.e., a fabric 1, that is provided on its first side 1a with a dyed biopolymer layer, i.e., with a biopolymer layer 4 which includes dye molecules 5. For example, the fabric 1 may be a woven fabric, e.g., a denim fabric, which is provided with a biopolymer layer 4 comprising bacterial cellulose that is dyed, preferably indigo dyed.

In other words, the support material, i.e., the fabric 1, is provided with a dyed biopolymer layer, preferably with a indigo-dyed bacterial cellulose layer. Another embodiment of the present invention is schematically shown in FIGS. 2A, 2B and 2C, which illustrate an embodiment of the process of the present invention wherein the biopolymer-producing microorganisms 2 and the dye-producing microorganisms 3 are provided to the support material 1 separately, i.e., sequentially.

Figure 2A:
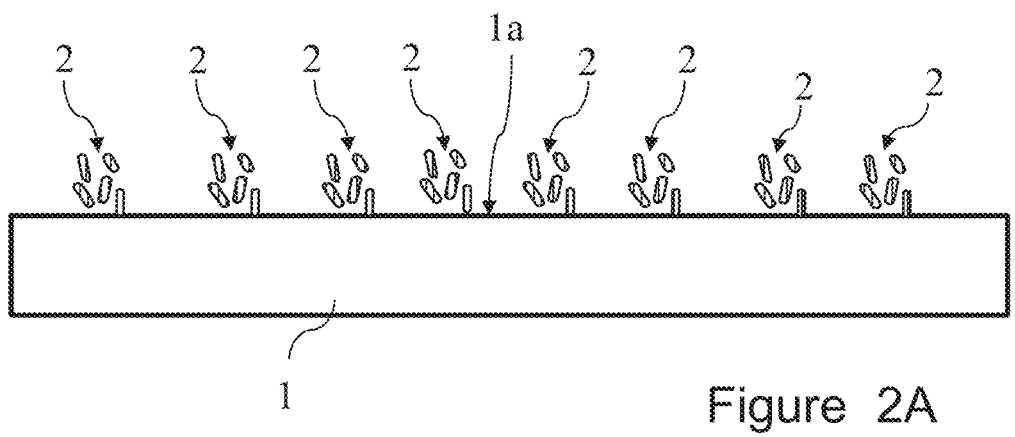
FIGS. 2A, 2B and 2C schematically show an embodiment of the process of the present invention wherein the biopolymer-producing microorganisms and the dye-producing microorganisms are provided to a support material separately, i.e., sequentially.
Figure 2B:
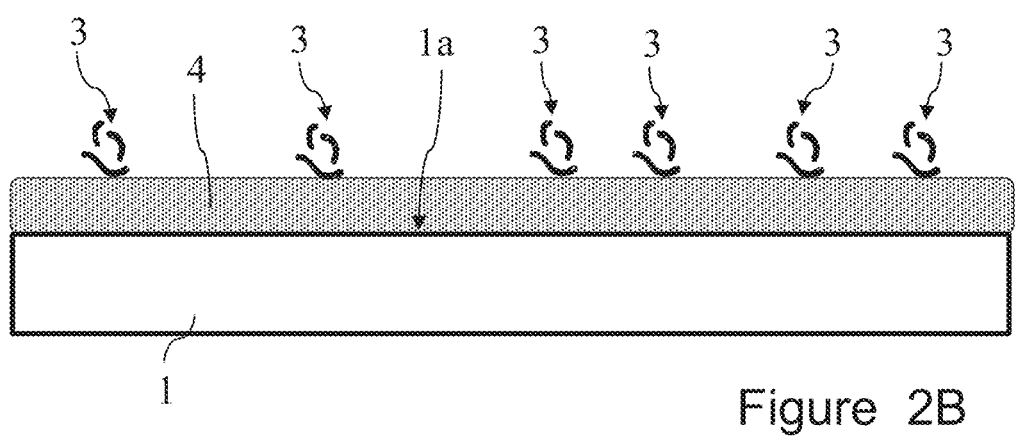
Figure 2C:
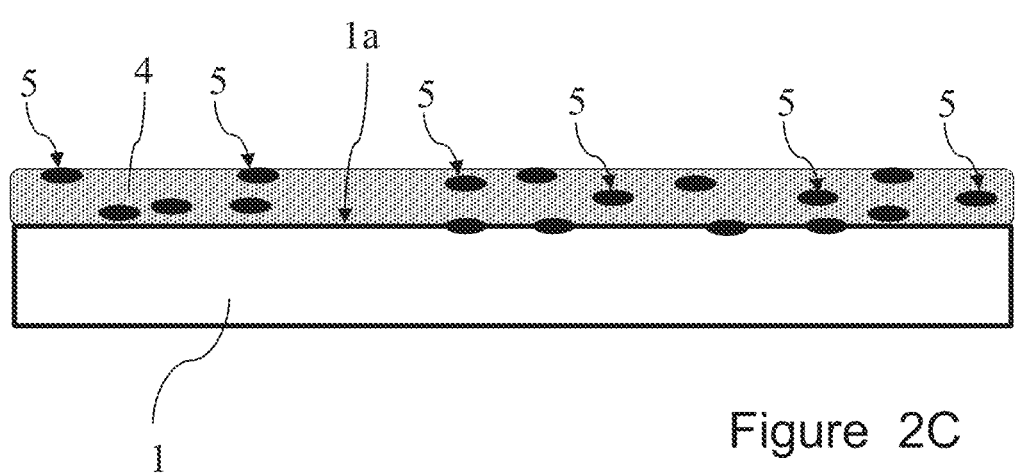

In the present FIGS. 2A-2C, the exemplary support material 1 is a textile article, in particular, is a fabric 1.

As above mentioned, biopolymer-producing microorganisms 2 are preferably *Gluconacetobacter* bacteria, which produce bacterial cellulose, and dye-producing microorganisms 3 are preferably recombinant *Escherichia coli*.

According to this embodiment of the invention, the process can be defined as a consecutive process, wherein the production of the biopolymer 4 and of the dye molecules 5 occurs substantially sequentially. A biopolymer layer 4 is provided to the first side 1a of a fabric 1 and, subsequently, a dye, i.e., dye molecules 5, is provided to said biopolymer layer 4, to obtain a dyed composite fabric according to a two-steps process.

As in FIGS. 1A-1B, the textile article of FIGS. 2A-2C is a fabric 1, preferably a woven fabric, shown according to a cross-sectional view.

According to this embodiment, the fabric 1 is contacted with biopolymer-producing microorganisms 2, i.e., with a culture comprising biopolymer-producing microorganisms 2, as shown in FIG. 2A.

The culture comprising biopolymer-producing microorganism 2 may be provided onto a first side 1a of the fabric 1 by conventional methods, such as spraying or pouring.

The fabric is subsequently incubated, preferably at a temperature ranging from 20° C. to 30° C., preferably ranging from 25° C. to 28° C. so that a layer of biopolymer may be formed directly on the first side 1a of the fabric 1. Preferably, the incubation is carried out at 28° C. At the end of the incubation, a composite fabric is provided, comprising the fabric 1 and a biopolymer layer 4.

Subsequently, as shown in FIG. 2B, at least part of the undyed biopolymer layer 4 is contacted with a culture comprising dye-producing microorganisms 3. For example, the culture comprising dye-producing microorganism 3 may be provided, or applied, to the undyed biopolymer layer 4 by conventional methods, such as spraying or pouring. A second incubation is then performed, preferably at a temperature ranging from 20° C. to 40° C. to allow the dye-producing microorganisms 3 to produce dye molecules directly on the undyed biopolymer layer 4, thus providing a dye, i.e., dye molecules 5, to at least part of the biopolymer layer 4. Accordingly, as shown in FIG. 2C, a dyed composite article, i.e., a dyed composite fabric, may be obtained, wherein the fabric 1 is provided with a biopolymer layer 4 which includes dye molecules 5, on its first side 1a.

The dyed composite article is subsequently optionally washed to remove the residual microorganisms, and dried.

According to embodiments, it may be not necessary to wait the end of the incubation to contact the undyed biopolymer layer 4 with a culture comprising dye-producing microorganisms 3. For example, a first, partial, incubation may be carried out, so that the biopolymer layer 4 is provided to the fabric 1 as thin layer. Subsequently, the culture comprising dye-producing microorganisms 3 can be inoculated onto the thin, partial, biopolymer layer, and incubated to produce dye molecules. In this case, the production of the biopolymer layer 4 may be continued, so that the production of the biopolymer layer 4 is completed substantially at the same time that the dye molecules are produced. As above discussed, in FIGS. 1A-1B and 2A-2C, reference is made to a fabric as support material; however, other support material may be used, such as, for example, paper, cardboard, wood, glass, plastic, and textile articles different from a fabric.

For example, when paper and/or cardboard is used as support material, the obtained dyed composite paper and/or dyed composite cardboard may be used to produce an article for packaging, for example a box, wherein the dyed biopolymer layer is the external visible surface of the article, i.e., of the box.

FIGS. 3A-3B and 4A-4C schematically show embodiments of the process for the production of a dyed biopolymer according to the invention. In particular, FIGS. 3A-3B and 4A-4C schematically show embodiments of the process for the production of a dyed biopolymer according to the invention wherein a support material is not used.

Figure 3A:
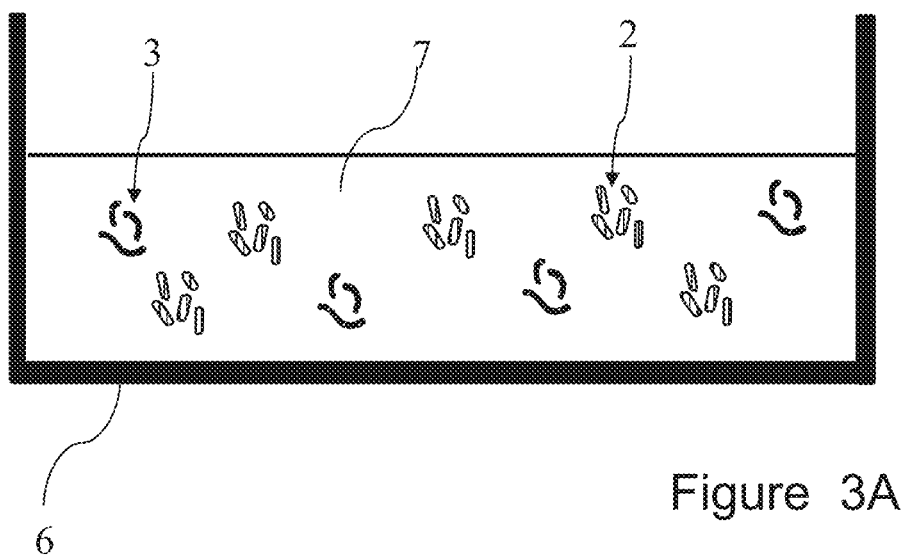
FIGS. 3A and 3B schematically show an embodiment of the process of the present invention wherein biopolymer-producing microorganisms and the dye-producing microorganisms are cultured together to obtain a dyed biopolymer.

FIG. 3A shows a container 6 containing a culture medium 7.

Figure 3B:
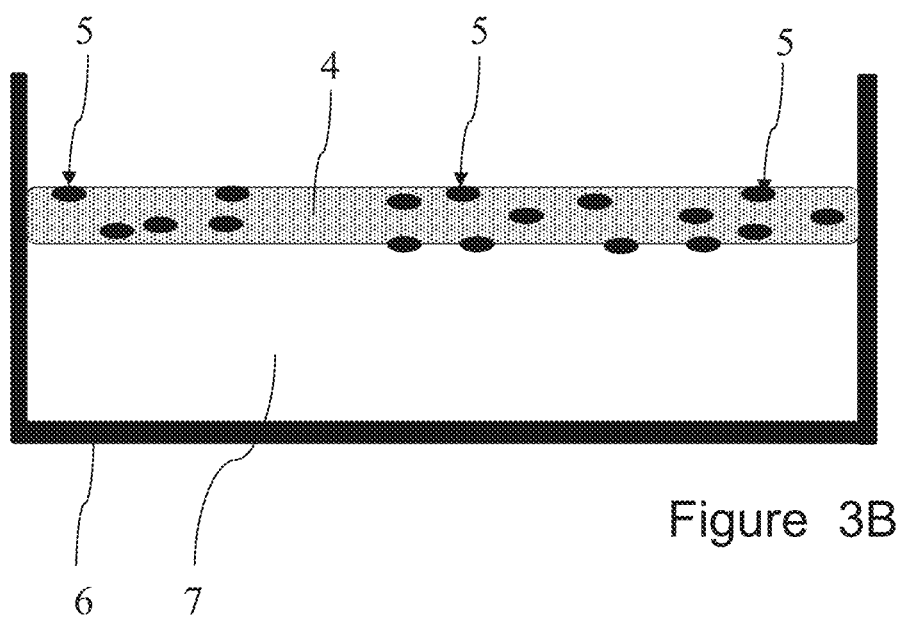

In the embodiment shown in FIGS. 3A and 3B, the culture medium 7 comprises required nutrients for both biopolymer-producing microorganisms 2 and dye-producing microorganisms 3. For example, the culture medium of said single culture may be obtained as a mixture of the two media used for the two microorganisms' growth and production, e.g., a mixture of Hestrin-Schramn (HS) medium and Terrific Broth (TB) medium.

For example, biopolymer-producing microorganisms 2 may be *Gluconacetobacter* bacteria, which produce bacterial cellulose, and dye-producing microorganisms 3 may be recombinant *Escherichia coli*, which may be used to produce indigo.

FIG. 3A schematically shows a container 6, wherein both biopolymer-producing microorganisms 2 and dye-producing microorganisms 3 are present in the same culture medium 7.

Biopolymer-producing microorganisms 2 and dye-producing microorganisms 3 are cultured together, i.e., co-cultured, to produce a biopolymer 4 including dye molecules 5.

Co-culture may be performed by incubating biopolymer-producing microorganisms 2 and dye-producing microorganisms 3, preferably at a temperature ranging from 20° C. to 40° C., to allow the production of a biopolymer and a dye.

FIG. 3B shows the container 6 of FIG. 3A, containing a dyed biopolymer, i.e., a biopolymer 4 including dye molecules 5 formed at the interface between air the culture medium 7.

Advantageously, by varying the shape of the container, the shape of the biopolymer may be varied.

The dyed biopolymer is subsequently extracted from the container, optionally washed to remove the residual microorganisms, and dried.

Figure 4A:
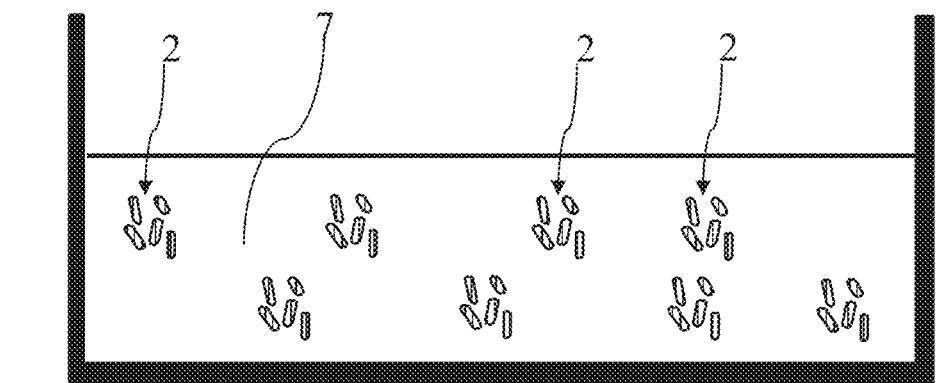
FIGS. 4A, 4B and 4C schematically show an embodiment of the process of the present invention wherein biopolymer-producing microorganisms are cultured sequentially to obtain a dyed biopolymer.
Figure 4B:
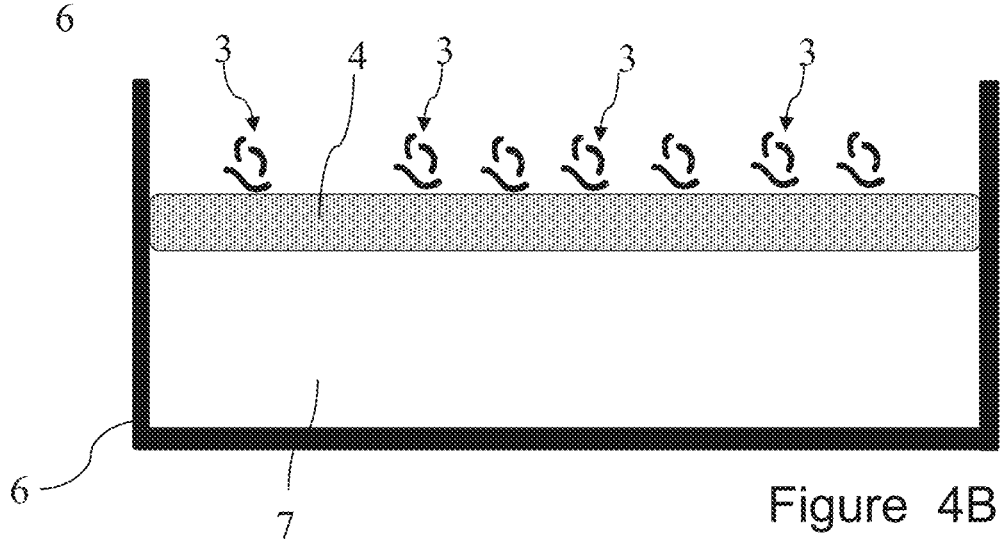
Figure 4C:
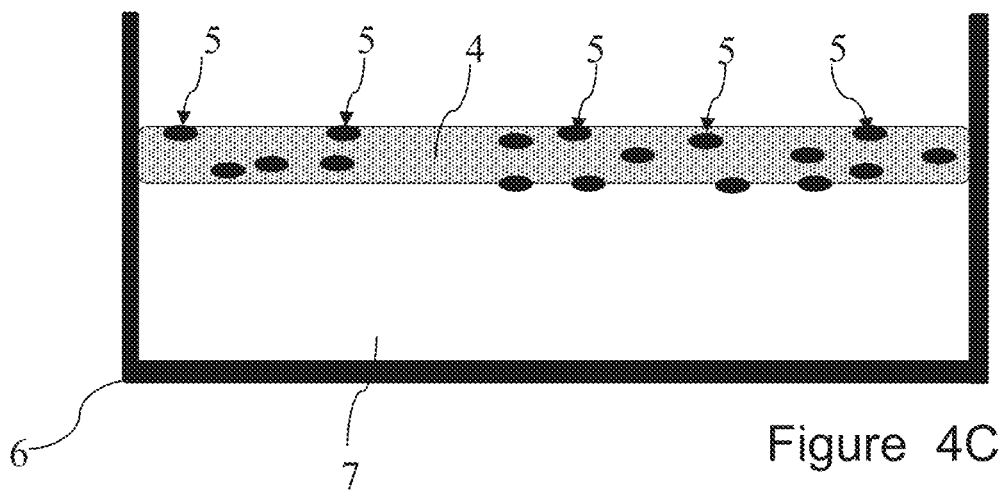

FIGS. 4A-4C schematically show an embodiment of the process for the production of a dyed biopolymer according to the invention wherein a support material is not used.

FIG. 4A shows a container 6, containing biopolymer-producing microorganisms 2 in a suitable culture medium 7.

For example, *Gluconacetobacter hansenii* bacteria may be used as biopolymer-producing microorganism. *Gluconacetobacter hansenii* may be cultured using Hestrin-Schramn (HS) medium. *Gluconacetobacter hansenii* may be cultured to produce bacterial cellulose.

Biopolymer-producing microorganisms are cultured in order to obtain a biopolymer 4 (e.g., a biopolymer layer 4).

Biopolymer-producing microorganisms are cultured by incubation, preferably at a temperature ranging from 20° C. to 30° C., more preferably ranging from 25° C. to 28° C., so that a layer of biopolymer 4 may be formed at the interface between air and the culture medium 7.

FIG. 4B shows the container 6 of FIG. 4A, after the incubation of the biopolymer producing microorganisms. The container 6 contains a biopolymer 4 which is not dyed, i.e., which does not include dye molecules, formed at the interface between air the culture medium 7. In FIG. 4B, the biopolymer 4 is contacted with dye-producing microorganisms 3.

Such dye-producing microorganisms 3 are then cultured to provide the biopolymer 4 with a dye, i.e., with dye molecules 5 (as shown in FIG. 4C).

For example, dye-producing microorganisms may recombinant *E. coli*. The dye produced may be indigo.

Dye-producing microorganisms 3 may be cultured by incubation, preferably at a temperature ranging from 20° C. to 40° C., so that dye molecules 5 are produced directly on the undyed biopolymer layer 4, to provide a dye, to at least part of the biopolymer layer 4.

FIG. 4C shows the container 6 of FIGS. 4A and 4B, containing a dyed biopolymer, i.e., a biopolymer 4 formed at the interface between air the culture medium 7, including dye molecules 5, at the end of the process.

As above mentioned, using containers of different shapes, biopolymers having different shape may be obtained.

The dyed biopolymer is subsequently extracted from the container, optionally washed to remove the residual microorganisms, and dried.

Figure 5A:
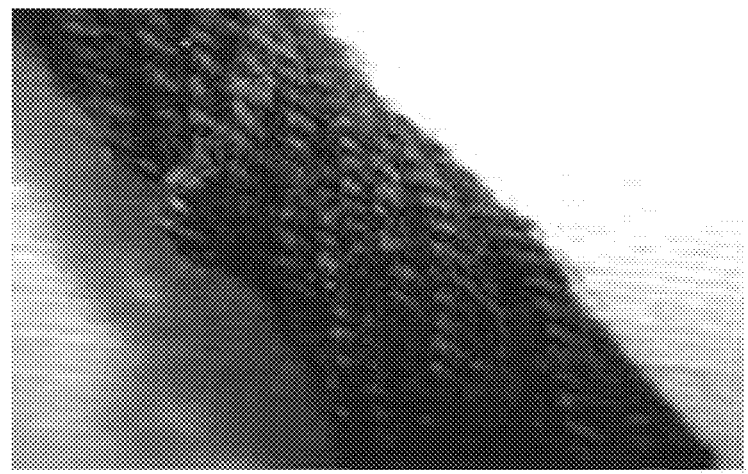
FIG. 5A shows a dyed composite article, in particular a dyed composite yarn, comprising a biopolymer dyed according to known methods.
Figure 5B:
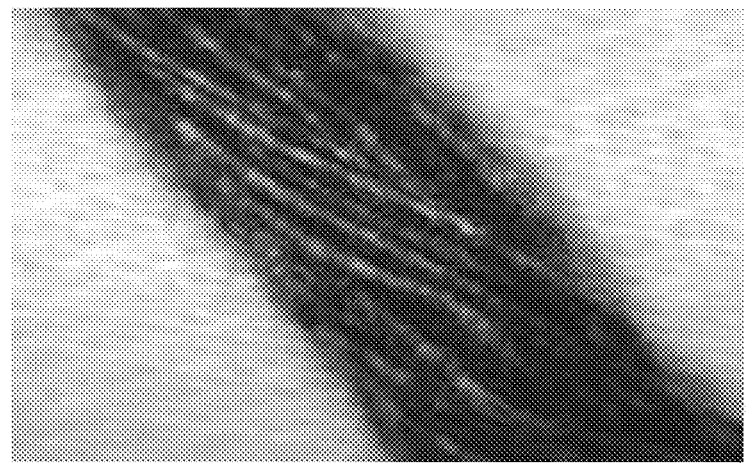
FIG. 5B shows a shows a dyed composite yarn comprising a dyed biopolymer according to the invention.

FIGS. 5A and 5B show a comparison between a dyed composite article, in particular a dyed composite yarn, obtained through known methods (FIG. 5A), and a dyed composite yarn obtained through the process of the invention (FIG. 5B).

FIG. 5A shows a yarn provided with a biopolymer and dyed with indigo, according to known techniques. As can be observed, the dyed composite yarn of FIG. 5A has an homogeneous distribution of the dye and a uniform distribution of the color, without shades.

Conversely, FIG. 5B shows a yarn provided with a biopolymer and dyed with indigo, according to the process of the invention. To obtain a dyed composite yarn according to FIG. 5B, a yarn is used as a support material, and provided with cultures comprising biopolymer producing microorganisms and dye producing microorganisms. For example, such cultures may be provided to the yarn at the same time (or substantially at the same time), so that biopolymer producing microorganisms and dye producing microorganisms are cultured together. In other examples, the above mentioned cultures may be provided to the yarn sequentially: a culture comprising biopolymer-producing microorganisms first, to provide the yarn with a biopolymer and subsequently a culture comprising dye-producing microorganisms to produce a dye, to dye at least part of the biopolymer.

According to embodiments, cultures comprising microorganisms can be provided to a yarn by impregnation or by continuous or discontinuous dispensing of the cultures to the yarn. A process for continuous or discontinuous dispensing of cultures comprising microorganisms to a yarn is disclosed, for example, in the International application number PCT/EP2018/065506, having title "A PROCESS FOR PROVIDING A CULTURE OF MICROORGANISMS TO A YARN", in the name of the present Applicant.

As can be observed, the dyed composite yarn of FIG. 5B shows a non-homogeneous and non-uniform distribution of the dye, and shows a plurality of shades of color (i.e., it has a multi-shaded appearance).

The dyed composite yarn of FIG. 5B can be, advantageously, used in the production of fabrics, garments and other textile articles. Advantageously, the use of dyed composite yarns according to the invention will provide different visual look to the fabric, garment or other article produced.

According to embodiments, the dyed composite yarn according the invention may be, advantageously, used as warp and/or weft yarn in a woven fabric.

Figure 6:
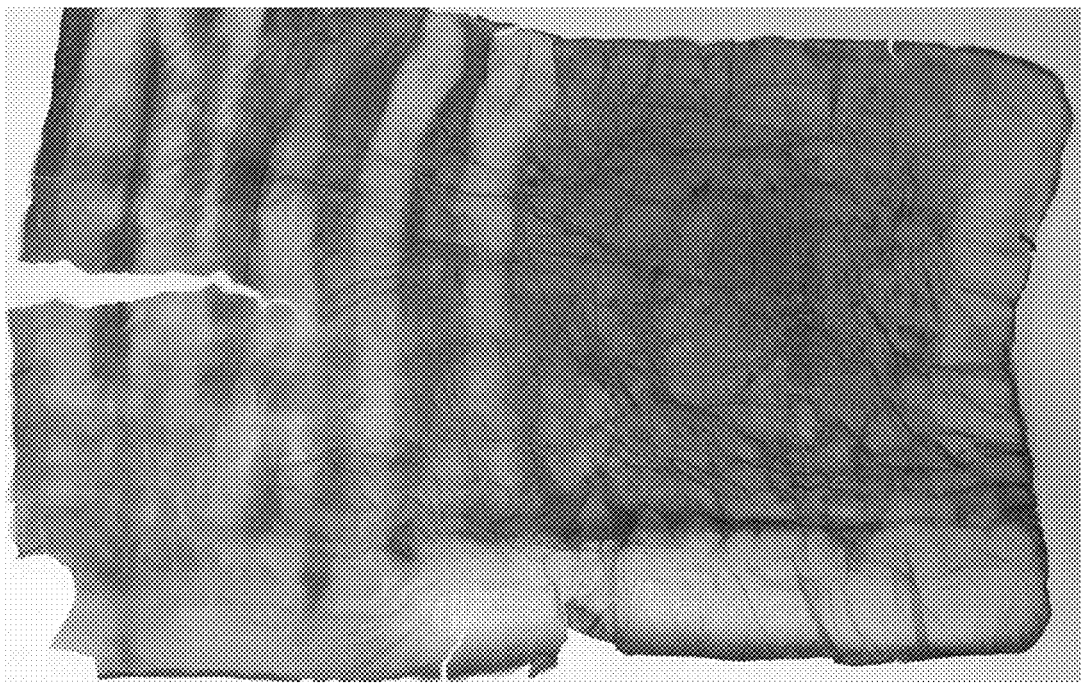
FIG. 6 shows an exemplary dyed biopolymer according to the invention.

FIG. 6 shows an exemplary dyed biopolymer according to the invention.

As can be observed, the dyed biopolymer of FIG. 6 has a non-uniform and non-homogeneous distribution of the dye.

According to embodiments, the dyed biopolymer of the invention (e.g., the exemplary dyed biopolymer of FIG. 6) may be worked in a plurality of articles. Exemplary articles are home decorations, fashion and home accessories, packaging articles and textile articles.

According to embodiments, the dyed biopolymer of the invention may be produced, i.e., grown onto a support material, to obtain a dyed composite article having a non-uniform and non-homogenoeus distribution of the dye, at least in the dyed biopolymer layer.

Advantageously, through the process of the invention a dyed biopolymer, as well as dyed composite articles comprising said biopolymer may be obtained, wherein at least part of the biopolymer layer presents a multi-shaded effect, which is not reproducible, i.e., which cannot be reproduced from a textile article to another.

Experimental Section

1) Concurrent Process (Co-Culture)—Dyed Composite Article

In the present example of "concurrent process", both biopolymer-producing microorganism, for example, bacterial cellulose producing bacteria (e.g., *Acetobacter* strains or *Gluconacetobacter* strains), and dye-producing microorganisms, e.g., dye molecule producing bacteria (e.g., recombinant *E. coli*), are grown together to produce a dyed bacterial cellulose layer directly on a support material, in particular a textile article, e.g., a fabric or a yarn.

In the present example *Gluconacetobacter hansenii* bacteria as biopolymer-producing microorganism, to produce bacterial cellulose, and recombinant *E. coli* as dye-producing microorganisms are used.

First, cultures are prepared for each bacteria. The cultures of each bacteria are incubated, so that bacteria grow separately in their optimum conditions as described below.

*Gluconacetobacter* culture: *Gluconacetobacter hanseii* is grown first in Hestrin-Schramn (HS) medium including glucose, bacto-peptone, yeast extract, disodium phosphate and citric acid. The culture is incubated at 26-28° C. until the cell number is about $3 \times 10^8$ cells/ml.

*E. coli* culture: A colony of recombinant *E. coli* is grown in antibiotic containing Terrific Broth (TB) including tryptone, yeast extract, glycerol and phosphate salts. The culture is incubated at 37° C. until the cell number is about $8 \times 10^8$ cells/ml.

Inoculation for concurrent process: For concurrent process TB and/or HS media can be used, regarding to the microorganisms requirements for the production of the biopolymer and the dye during cultivation, i.e., incubation.

To facilitate the production of both bacterial cellulose and dye molecules, recombinant *E. coli* can be used for each product with same medium, i.e., different strains of recombinant *E. coli* may be used to produce the biopolymer and the dye.

*Gluconacetobacter* and recombinant *E. coli* cultures are inoculated on the surface of a textile article, for example the first side of a fabric. The final cell number ratio between recombinant *E. coli* and *Gluconacetobacter* is preferably adjusted for inoculation (for example between 1:1 and 1:10; but preferred 1:4 and 1:5, respectively). After few hours (14-24 hours), arabinose or IPTG (Isopropyl β-D-1-thiogalactopyranoside) is added to the media to induce the recombinant *E. coli* cells to produce dye molecules. The textile article inoculated with *Gluconacetobacter* and recombinant *E. coli* cultures is incubated at 25° C.-30° C. for at least one week, so that the bacterial cellulose and dye molecules are produced on the textile article.

The dyed-bacterial cellulose coated textile article is washed with NaOH to remove all residual bacteria and impurities of growth media, and dried.

2) Consecutive Process—Dyed Composite Article

In "consecutive process", biopolymer producing microorganisms, e.g., bacterial cellulose producing bacteria (*Acetobacter* strains or *Gluconacetobacter* strains), and dye producing microorganisms, e.g., dye molecule producing bacteria (recombinant *E. coli*) may be grown separately, in their optimum conditions.

In the present example *Gluconacetobacter* bacteria as biopolymer-producing microorganism, to produce bacterial cellulose, and recombinant *E. coli* as dye-producing microorganisms are used.

In the present example, a textile article is used as support material.

First, *Gluconacetobacter* is directly grown onto a textile article, such as a fabric or a yarn, to produce bacterial cellulose (to provide the textile article with a bacterial cellulose layer), and then *E. coli* is added to produce the dye molecules.

*Gluconacetobacter* culture: *Gluconacetobacter hanseii* is grown first in Hestrin-Schramn (HS) medium including glucose, bacto-peptone, yeast extract, disodium phosphate and citric acid.

*E. coli* culture: A colony of recombinant *E. coli* is grown in antibiotic containing Terrific Broth (TB) including tryptone, yeast extract, glycerol and phosphate salts.

The *Gluconacetobacter* culture is added on the textile article for bacterial cellulose production and incubated on the textile article at 26° C.-28° C., preferably 28° C., for few days (for example 1-5 days). At the end of the incubation, a bacterial cellulose layer is obtained on the textile article.

The *E. coli* culture is incubated at 35° C.-40° C., preferably at 37° C., for few hours (14-24 hours), then IPTG (Isopropyl β-D-1-thiogalactopyranoside) or arabinose is added to induce the cells for dye molecule production. Then the culture is added on the bacterial cellulose layer on the textile article and incubated at 25° C.-30° C. for a time that is selected in order to obtain a biopolymer layer having a predetermined shade of color, as well as a predetermined thickness. Accordingly, the longer is the time of incubation, the thicker is the biopolymer layer obtained.

In this case, the thickness of the biopolymer layer increases because the *Gluconacetobacter* cells are still on the textile article when the culture of dye-producing *E. coli* is added on the bacterial cellulose layer on the textile article. After having provided the culture of dye-producing *E. coli* onto the bacterial cellulose layer on the textile article, an incubation is performed wherein both *E. coli* and *Gluconacetobacter* are grown.

The dye molecules may be produced on and/or in the bacterial cellulose layer. Both *Gluconacetobacter* and/or *E. coli* growth on the textile article may be repeated more than once, to produce different layers (for example, one on another) of dyed bacterial cellulose (namely, bio-dyed bacterial cellulose) to obtain additional different visual effects.

The dyed-bacterial cellulose coated textile article is washed with NaOH to remove all bacteria residues and impurities of growth medium from fabric/yarn, and dried.

3) Concurrent Process (Co-Culture)—Dyed Biopolymer

In the present example of "concurrent process", both biopolymer-producing microorganism, for example, bacterial cellulose producing bacteria (e.g., *Acetobacter* strains or *Gluconacetobacter* strains), and dye-producing microorganisms, e.g., dye molecule producing bacteria (e.g., recombinant *E. coli*), are grown together to produce a dyed bacterial cellulose.

In the present example, biopolymer-producing microorganism used are *Gluconacetobacter hanseii* bacteria, to produce bacterial cellulose, and dye-producing microorganisms used are recombinant *E. coli*, to produce a dye, e.g., indigo.

A culture is prepared for each bacteria, i.e. *Gluconacetobacter hansenii* and *E. coli*. The cultures of each bacteria are incubated, so that bacteria grow separately in their optimum conditions as described below.

*Gluconacetobacter* culture: *Gluconacetobacter hanseii* is grown in Hestrin-Schramn (HS) medium including glucose, bacto-peptone, yeast extract, disodium phosphate and citric acid. The culture is incubated at 26-28° C. until the cell number is about $3 \times 10^8$ cells/ml.

*E. coli* culture: A colony of recombinant *E. coli* is grown in antibiotic containing Terrific Broth (TB) including tryptone, yeast extract, glycerol and phosphate salts. The culture is incubated at 37° C. until the cell number is about $8 \times 10^8$ cells/ml.

Inoculation for concurrent process: as above mentioned, for concurrent process TB and/or HS media can be used, regarding to the microorganisms requirements for the production of the biopolymer and the dye during cultivation, i.e., incubation. For example, a single medium may be used to grow different strains of recombinant *E. coli*, for the production of both bacterial cellulose and dye molecules.

In the present example, the culture of *Gluconacetobacter* and the culture of recombinant *E. coli* cultures are mixed together, and the final cell number ratio between recombinant *E. coli* and *Gluconacetobacter* is preferably selected to be between 1:1 and 1:10; preferably between 1:4 and 1:5. After few hours (14-24 hours), arabinose or IPTG (Isopropyl β-D-1-thiogalactopyranoside) is added to the media to induce the recombinant *E. coli* cells to produce dye molecules. The co-culture of *Gluconacetobacter* and recombinant *E. coli* cultures is incubated at 25° C.-30° C. for at least one week, so that the bacterial cellulose and dye molecules are produced, to provide a dyed bacterial cellulose, e.g., an indigo-dyed bacterial cellulose.

The dyed bacterial cellulose is from the container wherein it has been grown, washed with NaOH to remove all residual bacteria and impurities of growth media, and dried.

4) Consecutive Process—Dyed Biopolymer

In the present example of "consecutive process", biopolymer producing microorganisms, e.g., bacterial cellulose producing bacteria (*Acetobacter* strains or *Gluconacetobacter* strains), and dye producing microorganisms, e.g., dye molecule producing bacteria (recombinant *E. coli*) are grown separately and sequentially, in their optimum conditions.

In the present example, *Gluconacetobacter* bacteria and recombinant *E. coli* are used, respectively, as biopolymer-producing microorganism, to produce bacterial cellulose, and as dye-producing microorganisms.

According to this exemplary embodiment "concurrent process" *Gluconacetobacter* is cultured first, to produce bacterial cellulose. Subsequently, *E. coli* is added to produce dye molecules.

*Gluconacetobacter* culture: *Gluconacetobacter hanseii* is grown in Hestrin-Schramn (HS) medium including glucose, bacto-peptone, yeast extract, disodium phosphate and citric acid.

*E. coli* culture: a colony of recombinant *E. coli* is grown in antibiotic containing Terrific Broth (TB) including tryptone, yeast extract, glycerol and phosphate salts.

The *Gluconacetobacter* culture is incubated at 26° C.-28° C., preferably 28° C., for few days (for example 1-5 days). At the end of the incubation, a bacterial cellulose layer is obtained at the interface between air and the medium.

The *E. coli* culture is incubated at 35° C.-40° C., preferably at 37° C., for few hours (14-24 hours), then IPTG (Isopropyl β-D-1-thiogalactopyranoside) or arabinose is added to induce the cells for dye molecule production. After induction with IPTG, the *E. coli* culture is added on the bacterial cellulose layer. The bacterial cellulose layer provided with the *E. coli* culture is incubated at 25° C.-30° C., for a time that is selected in order to obtain a biopolymer layer having a predetermined shade of color, as well as a predetermined thickness. Accordingly, the longer is the time of incubation, the thicker is the biopolymer layer obtained.

In this case, the thickness of the biopolymer layer increases because the bacterial cellulose layer is not washed, and *Gluconacetobacter* cells are still present when the culture of dye-producing *E. coli* is added on the bacterial cellulose layer. After having provided the culture of dye-producing *E. coli* onto the bacterial cellulose layer, an incubation is performed wherein both *E. coli* and *Gluconacetobacter* are grown.

The dye molecules may be produced on and/or in the bacterial cellulose layer. Both *Gluconacetobacter* and/or *E. coli* growth may be repeated more than once, to produce different layers (for example, one on another) of dyed bacterial cellulose (namely, bio-dyed bacterial cellulose) to obtain additional different visual effects.

The dyed-bacterial cellulose is washed with NaOH to remove all bacteria residues and impurities of growth medium, and dried.

The invention claimed is:

1. A process for the production of a dyed composite article comprising at least a layer of dyed biopolymer, comprising the following steps:
   a) providing at least one support material;
   b1) providing at least part of said support material with at least one biopolymer-producing microorganism by contacting at least part of said support material with at least one culture of microorganisms comprising said biopolymer-producing microorganism and culturing said biopolymer-producing microorganism to provide at least a biopolymer layer to said support material, wherein said microorganism produce said biopolymer layer on at least part of said support material; and
   b2) providing at least part of said support material with at least one dye-producing microorganism by contacting at least part of said support material including said biopolymer layer with at least one culture of microorganisms comprising said dye-producing microorganism and culturing said dye-producing microorganism to provide at least a dye to at least part of said biopolymer layer, wherein said microorganism produce said dye to dye at least part of said biopolymer layer, whereby a dyed composite article is obtained;
   wherein said biopolymer layer comprises a plurality of shades of a same color.

2. The process according to claim 1, wherein the cell-number ratio of said dye-producing microorganisms to said biopolymer-producing microorganisms, is in a range from 1:1 to 1:10.

3. The process according to claim 1, wherein said step b1) and/or b2) is performed more than once.

4. The process according to claim 1, wherein said biopolymer is selected from a sugar-based biopolymer and an amino acid-based biopolymer, or a mixture thereof.

5. The process according to claim 1, wherein said dye is selected from indigo dye, indigoid dye, pigment dye and mixtures thereof.

6. The process according to claim 5 wherein said indigoid dye is selected from 6,6'-dibromoindigo, 5-bromoindigo, 5,5'-dibromoindigo, 5,7,5',7'-tetrabromoindigo, 4,5,7,4',5'-pentabromoindigo, 4,5,6,4',5',6'-hexabromoindigo, 7,7'-dimethylindigo, 4,5,4',5'-tetrachloroindigo, and mixtures thereof, and wherein said pigment dye is selected from melanin, anthraquinone, xanthomonadin, indigoidine, astaxanthin, canthaxantin, cycloprodigiosin, granadaene, heptylprodigiosin, prodigiosin, pyocyanin, rubrolone, scytonemin, staphyloxanthin, tryptathrin, undecylprodigiosin, violacein, zeaxanthin, ankaflavin, lycopene, monascorubramin, naphtoquinone, riboflavin, rubropunctatin, β-carotene, torularhodin and mixtures thereof.

7. The process according to claim 1, wherein said support material is selected from paper, cardboard, wood, glass, plastic and a textile article.

8. The process according to claim 7, wherein said textile article is selected from a fiber, a yarn, a fabric, a woven fabric, a denim fabric and a garment comprising any of said fabrics.

9. The process according to claim 8, wherein said woven fabric comprises warp yarns and weft yarns woven together, and has a front side and a back side, wherein said warp yarns and at least one plurality of weft yarns form a base layer of said woven fabric, and wherein a plurality of warp yarns and/or at least one plurality of weft yarns form an additional layer of loop portions, or yarn under portions or over portions, on at least one of the sides of said woven fabric.

10. The process according to claim 8, wherein said woven fabric comprises warp yarns and weft yarns woven together, and has a front side and a back side, wherein said warp yarns and at least one plurality of weft yarns form a base layer of said woven fabric, and wherein a plurality of warp yarns or at least one plurality of weft yarns forms an additional layer of loop portions, or yarn under portions or over portions, on at least one of the sides of said woven fabric.

11. The process according claim 1, wherein said biopolymer-producing microorganism and/or said dye-producing microorganism is selected from bacteria, algae, yeast, fungi and mixtures thereof.

12. The process according to claim 1, wherein said biopolymer-producing microorganism and/or said dye-producing microorganism is either a wild type or a genetically modified microorganism.

13. A process according to claim 1, wherein said biopolymer-producing microorganism is selected from biopolymer-producing bacteria, biopolymer-producing algae, and mixture thereof.

14. The process according to claim 13, wherein said biopolymer-producing bacteria are selected from *Gluconacetobacter, Aerobacter, Acetobacter, Achromobacter, Agrobacterium, Azotobacter, Salmonella, Alcaligenes, Pseudomonas, Rhizobium, Sarcina,* Streptoccoccus, *Bacillus* genus, genetically modified *Escherichia coli*, and mixtures thereof, and wherein biopolymer-producing algae are selected from Phaeophyta, Rhodophyta, *Chrysophyta*, and mixture thereof.

15. The process according to claim 1, wherein said dye-producing microorganism is selected from dye-producing bacteria, dye-producing fungi and mixture thereof.

16. The process according to claim 15, wherein said dye-producing bacteria are selected from *Chromobacterium violaceum, Serratia marcescens,* Chriseobacteium sp., *Staphylococcus aureus, Streptomyces* sp., *Vibrio* sp., *Corynebacterium* genus, genetically modified *Escherichia coli*, and mixtures thereof, and wherein said dye-producing fungi are selected from *Penicillium, Talaromyces, Fusarium, Scytallidium, Trametes, Xanthomonas, Streptomyces, Aspergillus* and mixtures thereof.

17. The process according to claim 1, further comprising a step c) of washing said dyed composite article obtained after said step b1) and/or b2), to remove said biopolymer-producing microorganisms, and/or said dye-producing microorganisms.

18. A process for the production of a dyed composite article comprising at least a layer of dyed biopolymer, comprising the following steps:
   a) providing at least one support material;
   b1) providing at least part of said support material with at least one biopolymer-producing microorganism, wherein said microorganism produce at least a biopolymer layer on at least part of said support material; and
   b2) providing at least part of said support material with at least one dye-producing microorganism, wherein said microorganism produce a dye to dye at least part of said biopolymer layer,
   wherein said support material is provided with said biopolymer-producing microorganism and said dye-producing microorganism by contacting at least part of said support material with:
      at least one culture of microorganisms comprising at least one biopolymer-producing microorganism and—at least one culture of microorganisms comprising at least one dye-producing microorganism; and
   wherein said biopolymer-producing microorganism and said dye-producing microorganism are cultured together, whereby a dyed composite article is obtained;
   wherein said biopolymer layer comprises a plurality of shades of a same color.

* * * * *